(12) United States Patent  
Kimball et al.

(10) Patent No.: US 9,301,772 B2  
(45) Date of Patent: Apr. 5, 2016

(54) LOADING CARTRIDGE FOR SURGICAL INSTRUMENT END EFFECTOR

(75) Inventors: Cory G. Kimball, Cincinnati, OH (US); Daniel W. Price, Loveland, OH (US); William E. Clem, Bozeman, MT (US); William D. Dannaher, Suzhou (CN)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 938 days.

(21) Appl. No.: 13/484,547

(22) Filed: May 31, 2012

(65) Prior Publication Data

US 2013/0324998 A1  Dec. 5, 2013

(51) Int. Cl.
| | |
|---|---|
| A61B 17/32 | (2006.01) |
| A61B 17/00 | (2006.01) |
| A61B 19/00 | (2006.01) |

(52) U.S. Cl.
CPC . *A61B 17/320068* (2013.01); *A61B 17/320092* (2013.01); *A61B 2017/0046* (2013.01); *A61B 2019/4857* (2013.01)

(58) Field of Classification Search
CPC .............. A61B 17/320068; A61B 17/320092; A61B 2017/0046; A61B 2019/4857
See application file for complete search history.

(56) References Cited

U.S. PATENT DOCUMENTS

| | | | |
|---|---|---|---|
| 5,980,510 A | 11/1999 | Tsonton et al. | |
| 6,500,176 B1 | 12/2002 | Truckai et al. | |
| 6,783,524 B2 | 8/2004 | Anderson et al. | |
| 7,159,494 B2 | 1/2007 | Jamnia et al. | |
| 7,416,101 B2 | 8/2008 | Shelton, IV et al. | |
| 7,658,740 B2 | 2/2010 | Shores et al. | |
| 7,738,971 B2 | 6/2010 | Swayze et al. | |
| 8,114,104 B2 | 2/2012 | Young et al. | |
| 2003/0199794 A1 | 10/2003 | Sakurai et al. | |
| 2006/0079874 A1 | 4/2006 | Faller et al. | |
| 2006/0123958 A1* | 6/2006 | Jamnia et al. | 81/467 |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0143797 A1 | 6/2009 | Smith et al. | |
| 2009/0209990 A1 | 8/2009 | Yates et al. | |
| 2010/0069940 A1 | 3/2010 | Miller et al. | |

(Continued)

FOREIGN PATENT DOCUMENTS

| | | |
|---|---|---|
| WO | WO 9724073 | 7/1997 |
| WO | WO 2010/126128 | 11/2010 |

OTHER PUBLICATIONS

International Search Report dated Sep. 26, 2013 for Application No. PCT/US2013/042672.

(Continued)

*Primary Examiner* — Amanda Patton  
(74) *Attorney, Agent, or Firm* — Frost Brown Todd LLC

(57) ABSTRACT

A surgical instrument includes a body assembly and a selectively coupleable end effector assembly. The end effector assembly may include a transmission assembly, an end effector, and a rotational knob operable to rotate the transmission assembly and the end effector. The body assembly includes a trigger and a casing having a distal aperture configured to receive a portion of the end effector assembly. First and second coupling assembly portions cooperatively couple the end effector assembly to the body assembly for use. An attachment assembly may be used to rotatably couple the first and second coupling assembly portions.

20 Claims, 12 Drawing Sheets

(56) References Cited

U.S. PATENT DOCUMENTS

2011/0015660 A1 1/2011 Wiener et al.
2011/0087218 A1 4/2011 Boudreaux et al.

OTHER PUBLICATIONS

International Preliminary Report on Patentability dated Dec. 2, 2014 and Written Opinion dated Sep. 26, 2013 for Application No. PCT/US2013/042672.

* cited by examiner

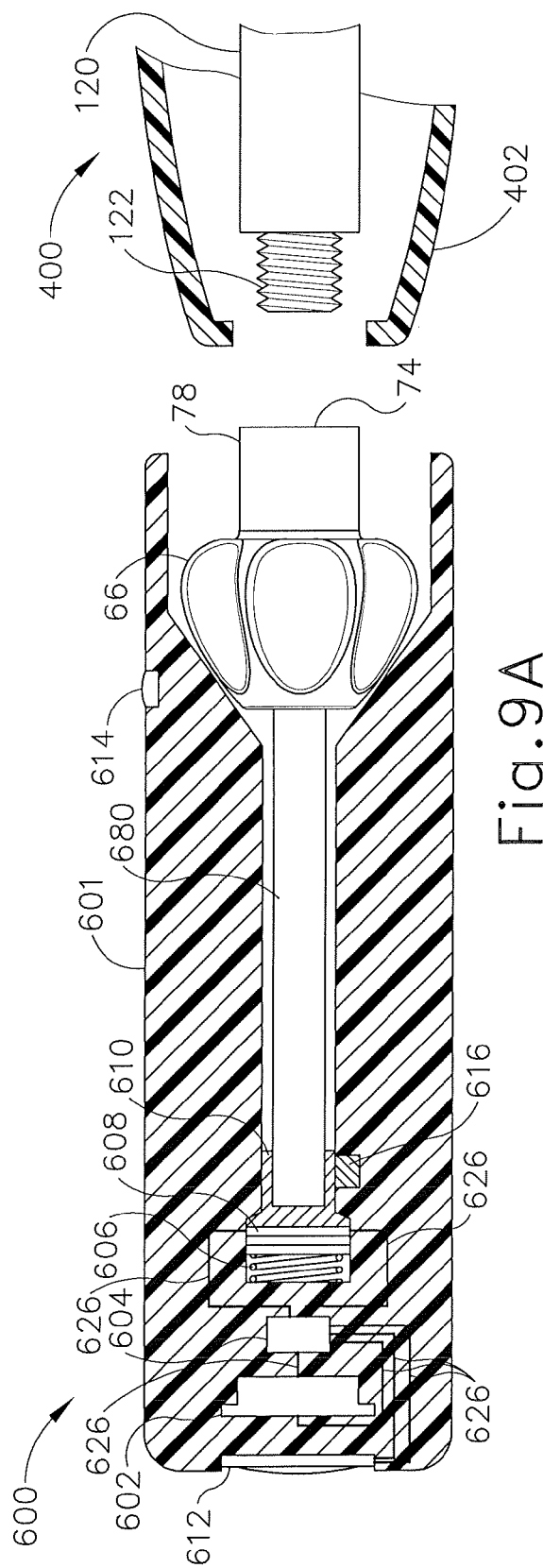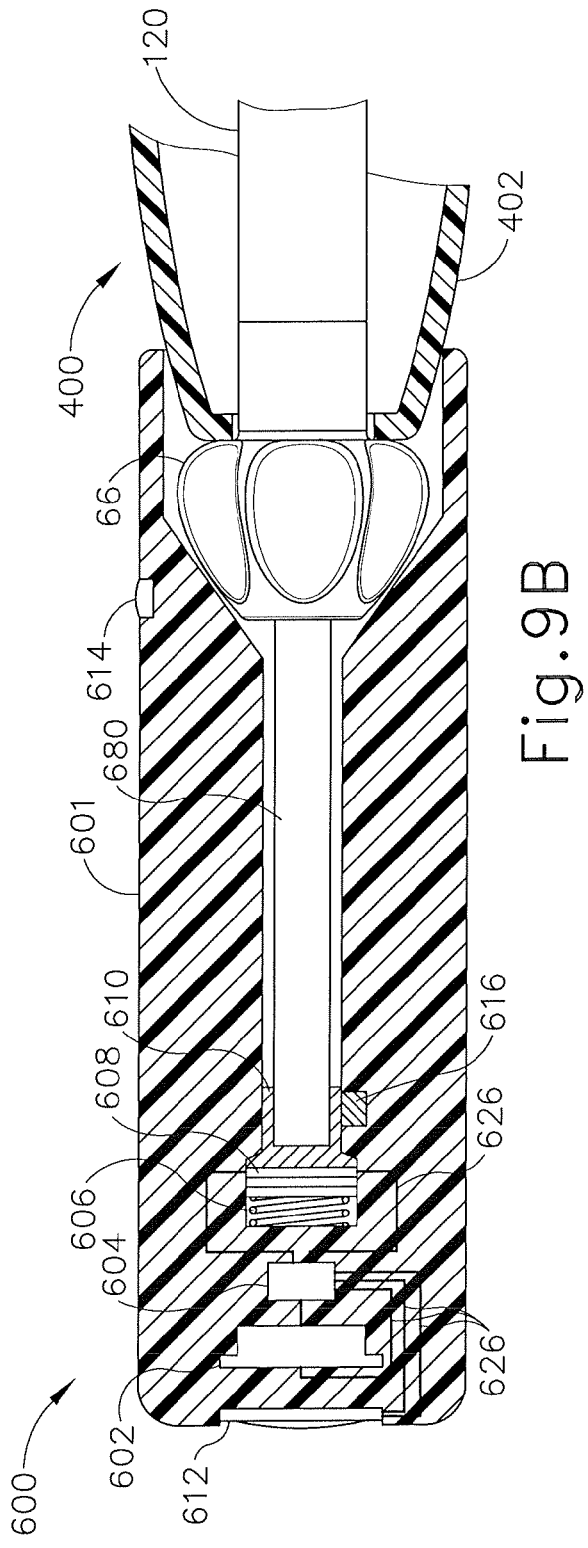

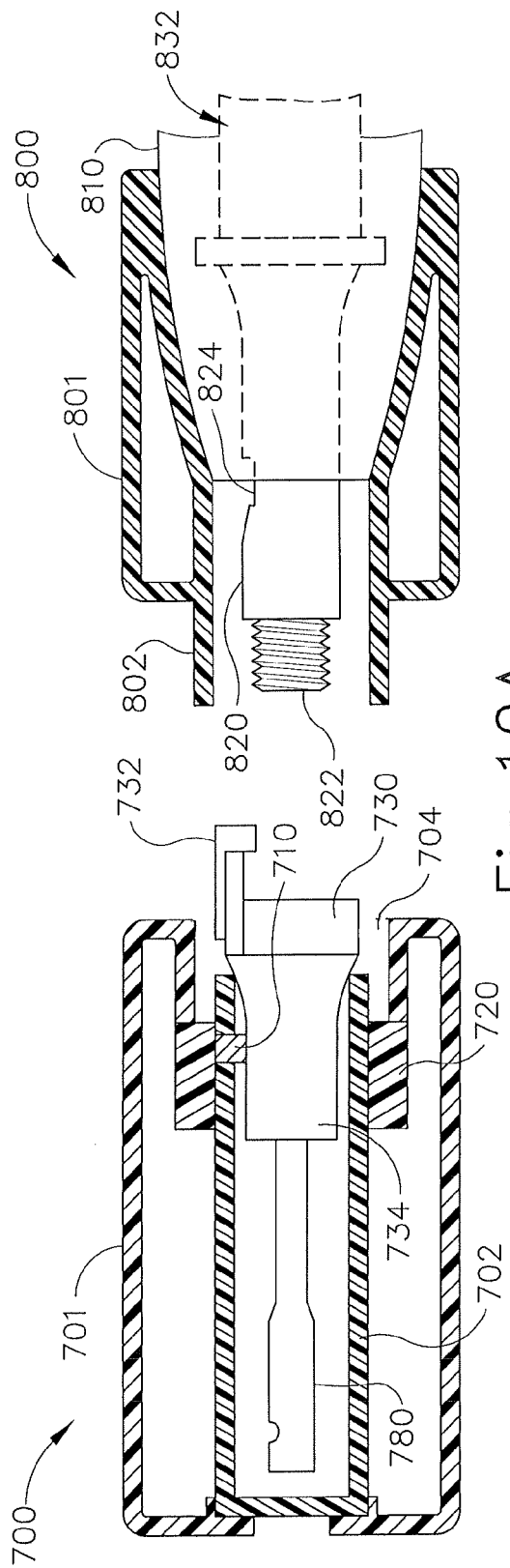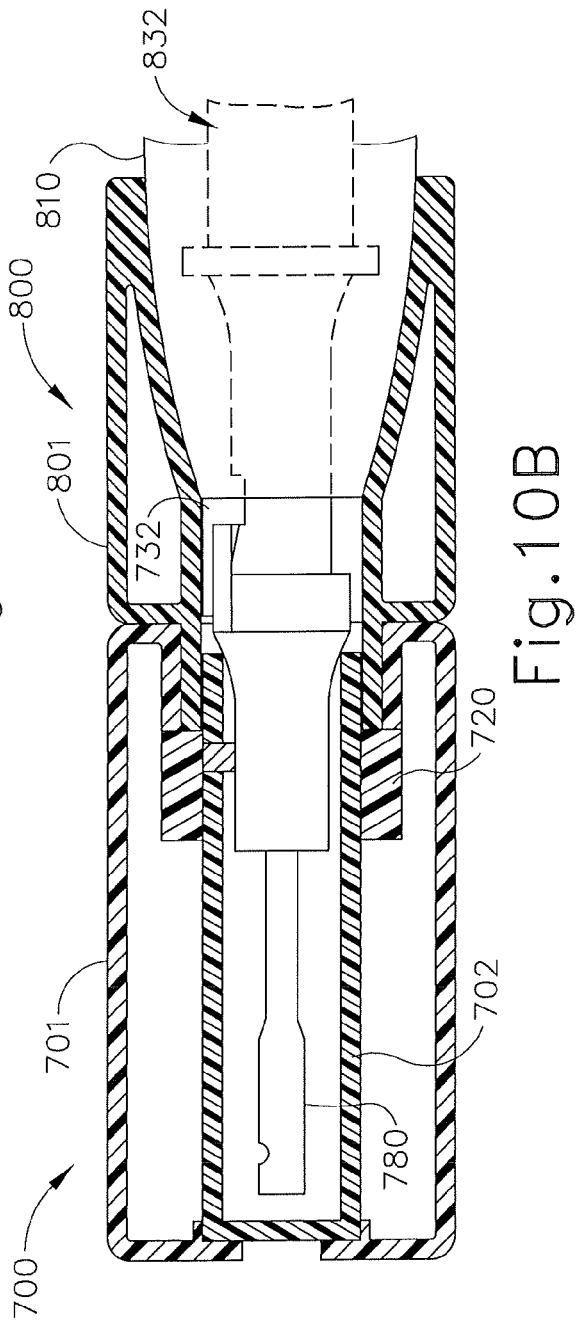

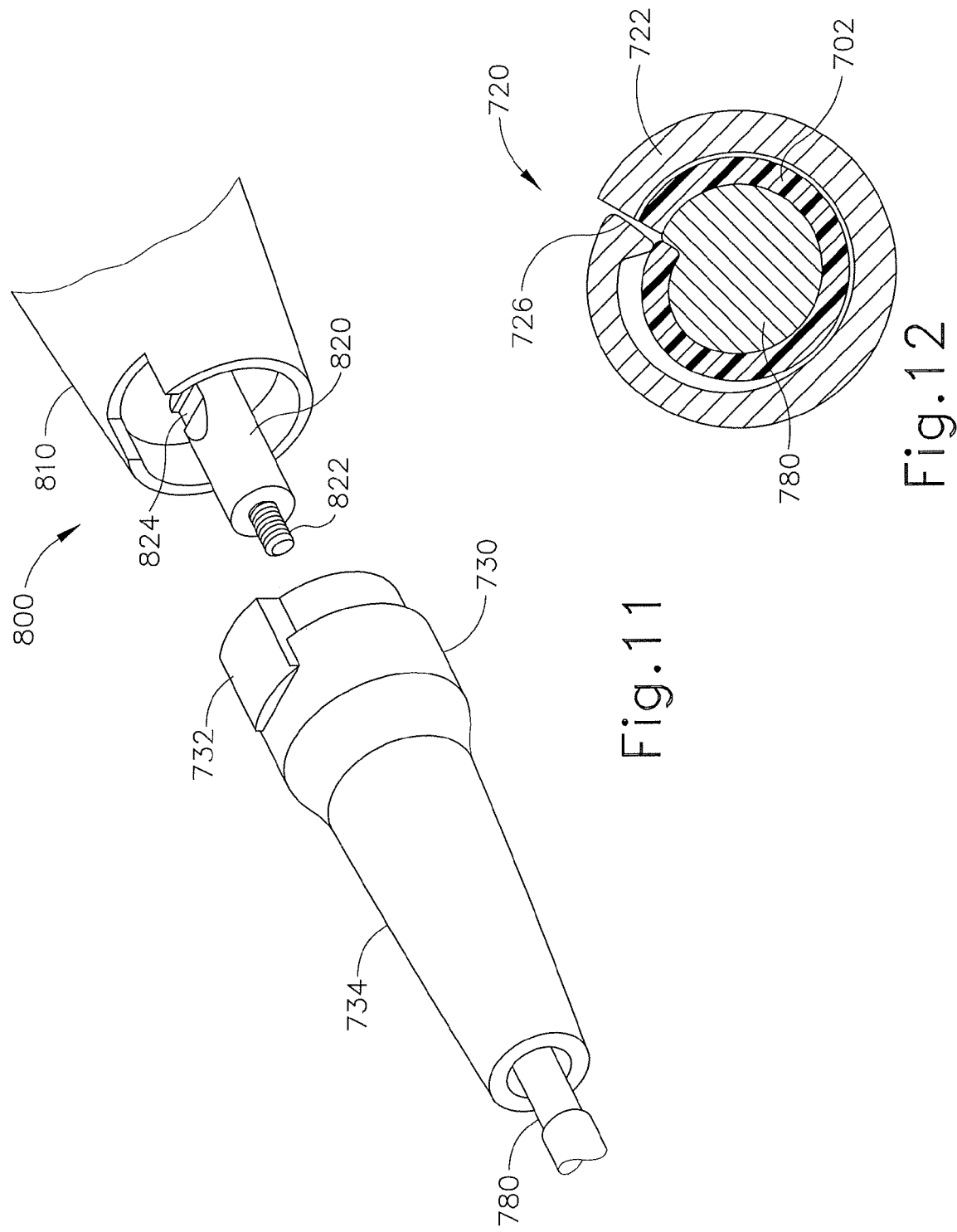

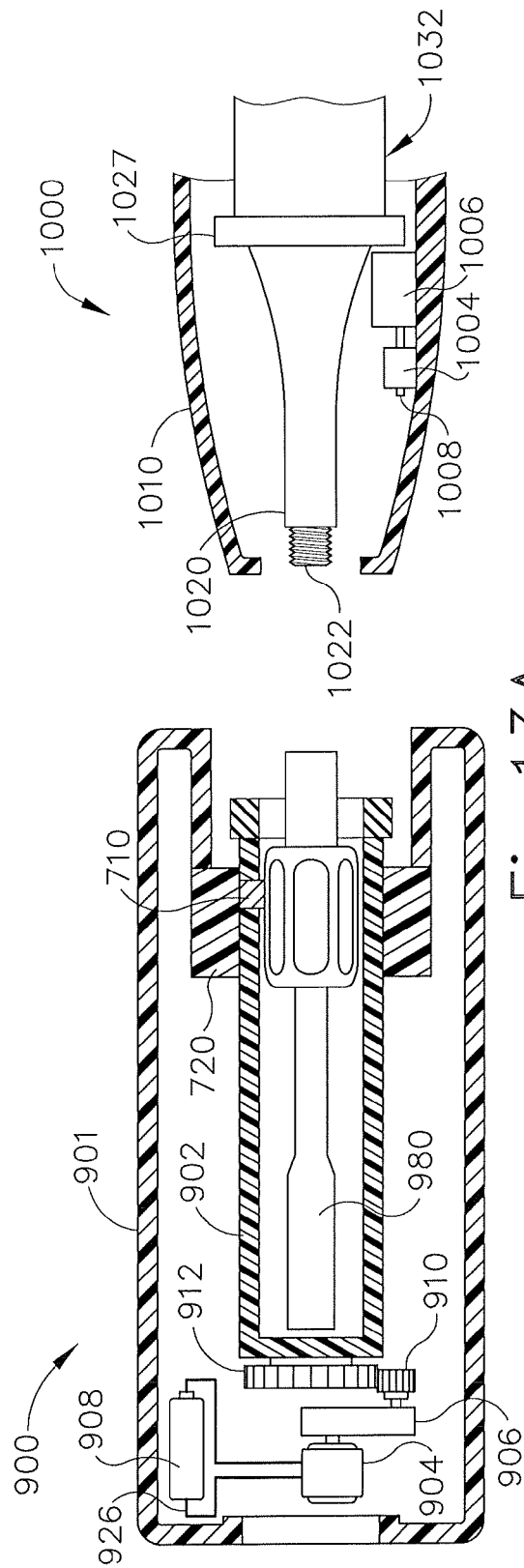
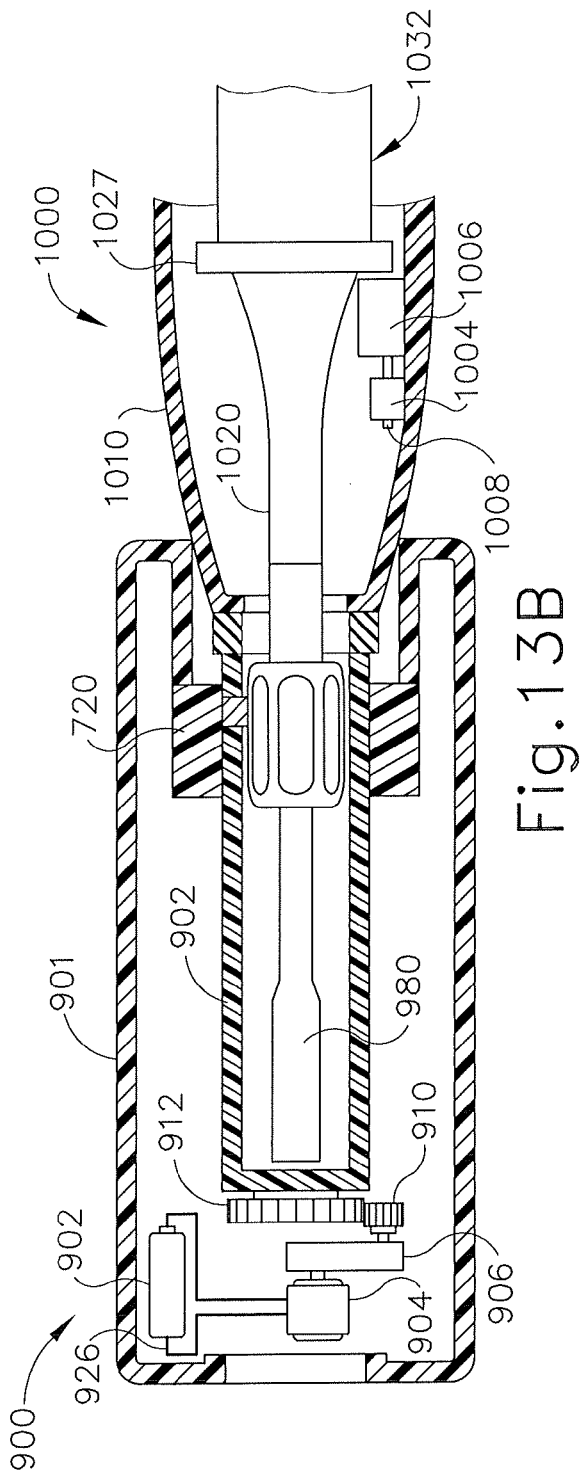
Fig. 13A
Fig. 13B

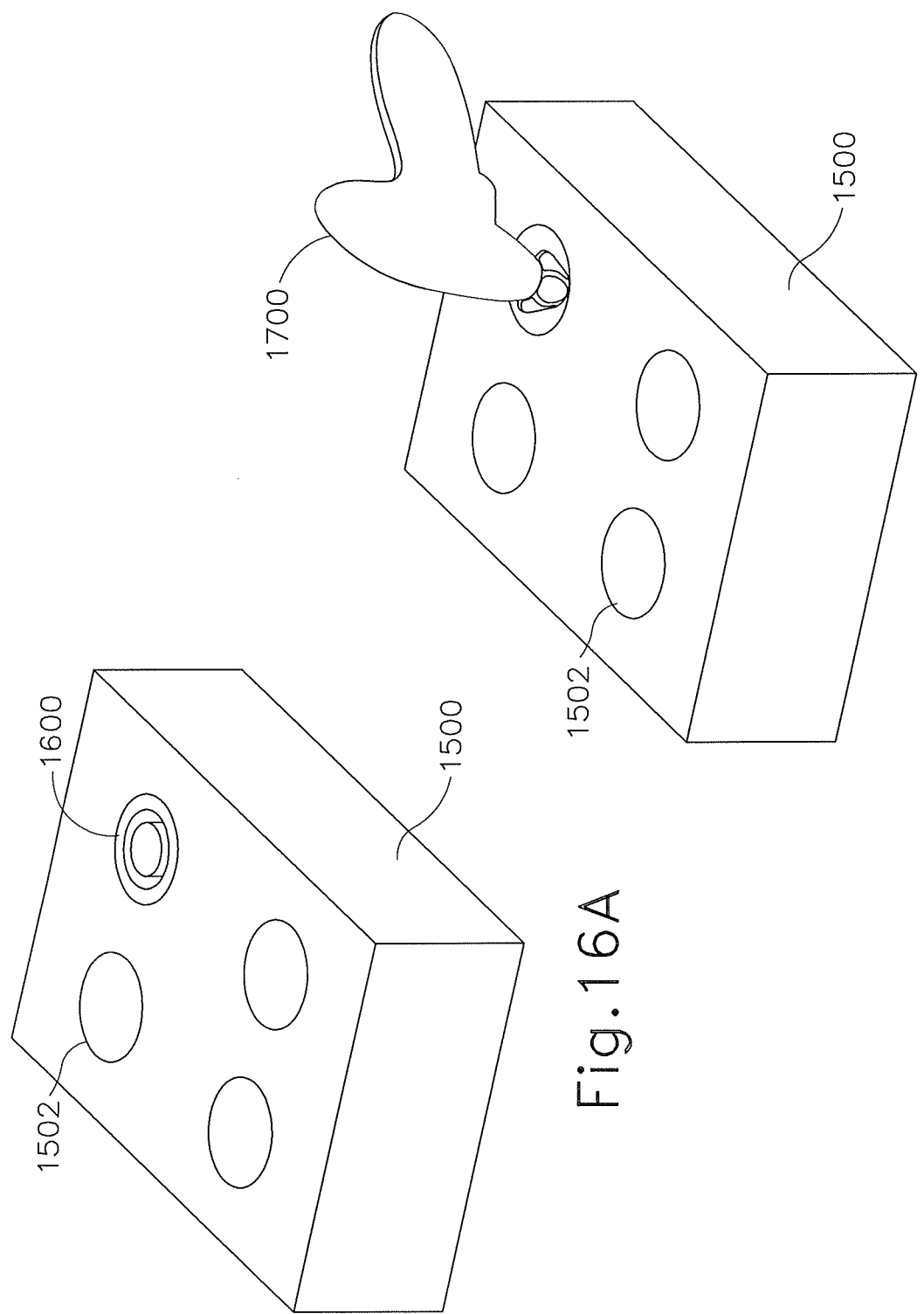

LOADING CARTRIDGE FOR SURGICAL INSTRUMENT END EFFECTOR

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pat. Pub. No. 2009/0209990 entitled "Motorized Surgical Cutting and Fastening Instrument Having Handle Based Power Source," published Aug. 20, 2009, now U.S. Pat. No. 8,657,174, issued Feb. 25, 2014, the disclosure of which is incorporated by reference herein; U.S. Pat. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004, the disclosure of which is incorporated by reference herein.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 9A depicts a side cross section view of an exemplary end effector assembly cartridge detached from a handle assembly of a surgical instrument;

FIG. 9B depicts a side cross section view of the end effector assembly cartridge of FIG. 9A attached to a handle assembly;

FIG. 10A depicts a side cross section view of another exemplary end effector assembly cartridge detached from a handle assembly;

FIG. 10B depicts a side cross section view of the end effector assembly cartridge of FIG. 10A attached to a handle assembly;

FIG. 11 depicts a partial perspective view of a blade collar detached from a handle assembly;

FIG. 12 depicts a cross section view of an exemplary torque collar around an end effector assembly;

FIG. 13A depicts a side cross section view of another exemplary end effector assembly cartridge detached from a handle assembly;

FIG. 13B depicts a side cross section view of the end effector assembly cartridge of FIG. 13A attached to a handle assembly;

FIG. 16A depicts a perspective view of an exemplary end effector assembly container holding an end effector assembly;

FIG. 16B depicts a perspective view of the end effector assembly container in FIG. 16A with a surgical instrument attaching to the end effector assembly;

Figure 1:
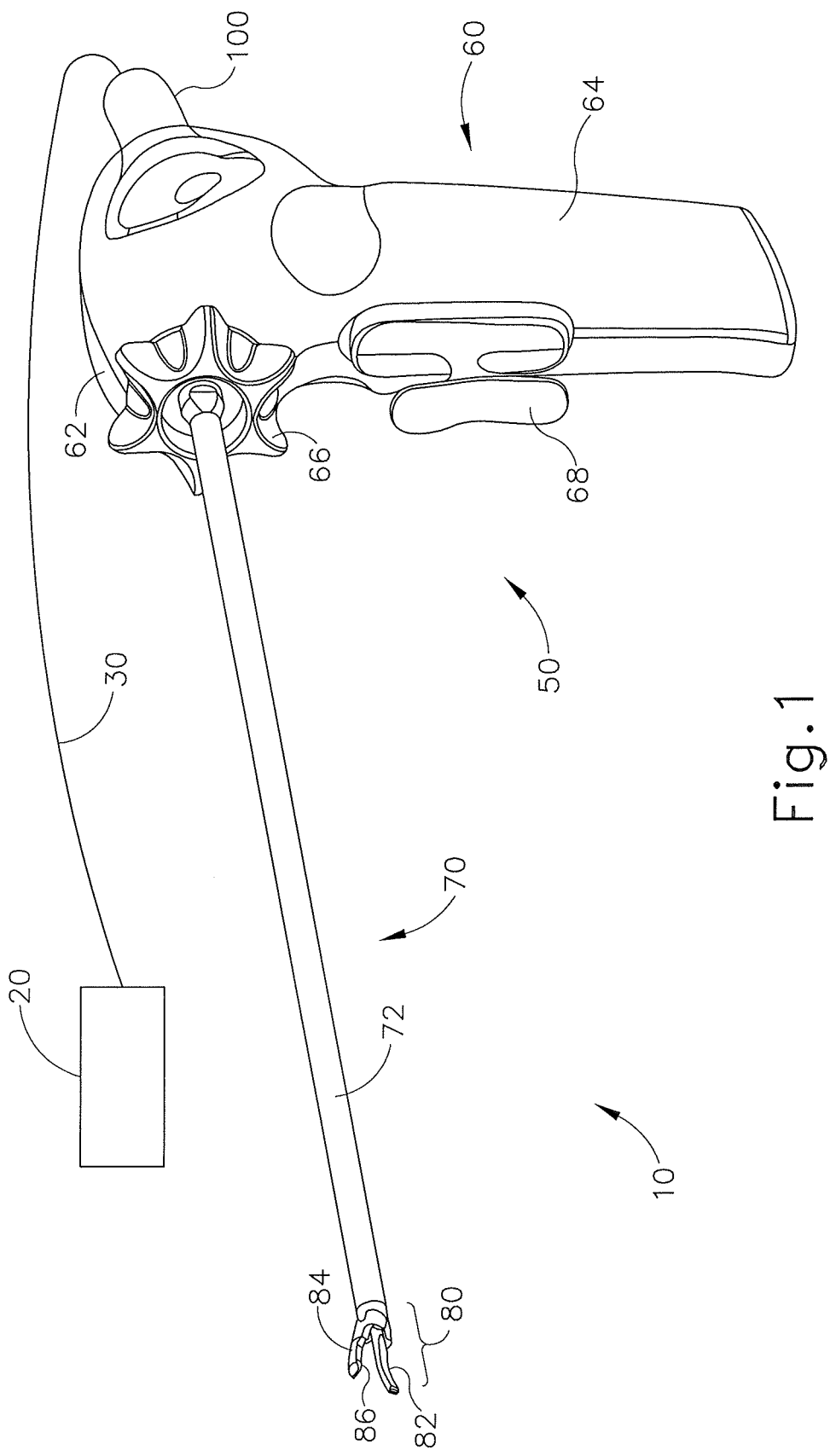
FIG. 1 depicts a perspective view of an exemplary surgical system having a surgical instrument and a generator.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

Various embodiments are directed to improved ultrasonic surgical instruments configured for effecting tissue dissecting, cutting, and/or coagulation during surgical procedures. In some versions, an ultrasonic surgical instrument apparatus is configured for use in open surgical procedures, but has applications in other types of surgery, such as laparoscopic, endoscopic, and robotic-assisted procedures. Versatile use is facilitated by selective use of ultrasonic energy.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

The various examples will be described in combination with an ultrasonic instrument as described herein. Such description is provided by way of example, and not limitation, and is not intended to limit the scope and applications thereof. For example, any one of the described embodiments is useful in combination with a multitude of ultrasonic instruments including those described in, for example, U.S. Pat. No. 6,783,524, entitled "Robotic Surgical Tool with Ultrasound Cauterizing and Cutting Instrument," filed on Apr. 18, 2002; US Pat. Pub. No. 2006/0079874, entitled "Tissue Pad for Use with an Ultrasonic Surgical Instrument," filed on Oct. 7, 2005; US Pat. Pub. No. 2007/0191713, entitled "Ultrasonic Device for Cutting and Coagulating," filed on Oct. 11, 2006; and US Pat. Pub. No. 2007/0282333, entitled "Ultrasonic Waveguide and Blade," filed on May 22, 2007, the disclosures of which are herein incorporated by reference.

As will become apparent from the following description, it is contemplated that embodiments of the surgical instrument described herein may be used in association with an oscillator module of a surgical system, whereby ultrasonic energy from the oscillator module provides the desired ultrasonic actuation for the present surgical instrument. It is also contemplated that embodiments of the surgical instrument described herein may be used in association with a signal generator module of a surgical system, whereby electrical energy in the form of radio frequencies (RF), for example, is used to provide feedback to the user regarding the surgical instrument. The ultrasonic oscillator and/or the signal generator modules may be non-detachably integrated with the surgical instrument or may be provided as separate components, which can be electrically attachable to the surgical instrument.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Ultrasonic Surgical System

FIG. 1 shows an exemplary ultrasonic surgical system (10) comprising an ultrasonic surgical instrument (50), generator (20), and a cable (30) coupling generator (20) to surgical instrument (50). In the present example, a suitable generator (20) comprises the GEN 300 sold by Ethicon Endo-Surgery, Inc. of Cincinnati, Ohio, but any suitable generator (20) may be used as would be apparent to one of ordinary skill in the art in view of the teachings herein. By way of example only, generator (20) may be constructed in accordance with the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should be noted that surgical instrument (50) will be described in reference to an ultrasonic surgical instrument; however, the technology described below may be used with a variety of surgical instruments, including, but not limited to, endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example, transmission assembly (70) is configured to be an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, and U.S. Pat. Pub. No. 2008/0200940, entitled "Ultrasonic Device for Cutting and Coagulating," published Aug. 21, 2008, the disclosures of which are incorporated by reference herein. Transmission assembly (70) of the present example comprises an outer sheath (72), an inner tubular actuating member (not shown), a waveguide (76), and an end effector (80) located on the distal end of transmission assembly (70). In the present example, end effector (80) comprises a blade (82) coupled to the waveguide (76), a clamp arm (84) operable to pivot at the proximal end of transmission assembly (70), and, optionally, one or more clamp pads (86) coupleable to clamp arm (84). End effector (80) and transmission assembly (70) will be discussed in greater detail below in reference to the example shown in FIG. 4. It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. The waveguide, which is adapted to transmit ultrasonic energy from a transducer (100) to blade (82), may be flexible, semi-flexible, or rigid. One merely exemplary ultrasonic transducer (100) is Model No. HP054, sold by Ethicon Endo-Surgery, Inc. of Cincinnati, Ohio. The waveguide may also be configured to amplify the mechanical vibrations transmitted through the waveguide to blade (82) as is well known in the art. The waveguide may further have features to control the gain of the longitudinal vibration along the waveguide and features to tune the waveguide to the resonant frequency of the system.

In the present example, the distal end of the blade (82) is disposed near an anti-node in order to tune the acoustic assembly to a preferred resonant frequency $f_o$ when the acoustic assembly is not loaded by tissue. When transducer (100) is energized, the distal end of blade (82) is configured to move longitudinally in the range of, for example, approximately 10 to 500 microns peak-to-peak, and preferably in the range of about 20 to about 200 microns at a predetermined vibratory frequency $f_o$ of, for example, 55.5 kHz. When transducer (100) of the present example is activated, these mechanical oscillations are transmitted through the waveguide to end effector (80). In the present example, blade (82), being coupled to the waveguide, oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (100) have been described, still other suitable configurations for transmission assembly (70) and transducer (100) will be apparent to one or ordinary skill in the art in view of the teachings herein.

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). A rotation knob (66) is shown in the present example to rotate transmission assembly (70) and transducer (100), but it should be understood that rotation knob (66) is merely optional. Mating housing portion (62) will be discussed in greater detail below in reference to FIG. 2. Lower portion (64) of multi-piece handle assembly (60) shown in FIG. 1 includes a trigger (68) and is configured to be grasped by a user using a single hand. One merely exemplary alternative configuration for lower portion (64) is depicted in FIG. 1 of U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein. Toggle buttons (69), shown in FIG. 2 of the present disclosure, are located on a distal surface of lower portion (64) and are operable to activate transducer (100) at different operational levels using generator (20). For instance, a first toggle button (69) may activate transducer (100) at a maximum energy level while a second toggle button (69) may activate transducer (100) at a minimum, non-zero energy level. Of course, toggle buttons (69) may be configured for energy levels other than a maximum and/or minimum energy level as will be apparent to one of ordinary skill in the art in view of the teachings herein. While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as separate toggle buttons (69) (which, in some versions may be operable either by a user's hand or foot) and a separate mating housing portion (62). Toggle buttons (69) are operable to activate transducer (100) and may be remote from mating housing portion (62). Multi-piece handle assembly (60) may be constructed from a durable plastic (such as polycarbonate or a liquid crystal polymer), ceramics and/or metals or any other suitable material as will be apparent to one of ordinary skill in the art in view of the teachings herein. Still other configurations for multi-piece handle assembly (60) will be apparent to those of ordinary skill in the art in view of the teachings herein.

II. Exemplary Coupling Assemblies for Ultrasonic Surgical Instrument

In some instances it may be useful to detach transmission assembly (70) from multi-piece handle assembly (60) and transducer (100). For instance, a detachable transmission assembly (70) may permit the reuse of multi-piece handle assembly (60) with multiple transmission assemblies (70) having various end effectors (80). By way of example only, the various end effectors (80) may have different sized and/or shaped blades (82) or the various end effectors (80) may have entirely different functions, such as RF end effectors, stapling end effectors, cutting end effectors, etc. Furthermore, a single multi-piece handle assembly (60) may be reused for different operations by a user by removing a dirty transmission assembly (70), optionally cleaning multi-piece handle assembly (60), and coupling a new transmission assembly (70) to multi-piece handle assembly (60) for a new operation. Accordingly, configuring multi-piece handle assembly (60) to couple to a variety of transmission assemblies (70) may be preferable for some users of surgical instrument (50).

A. Exemplary Multi-Piece Handle Assembly

Figure 2:
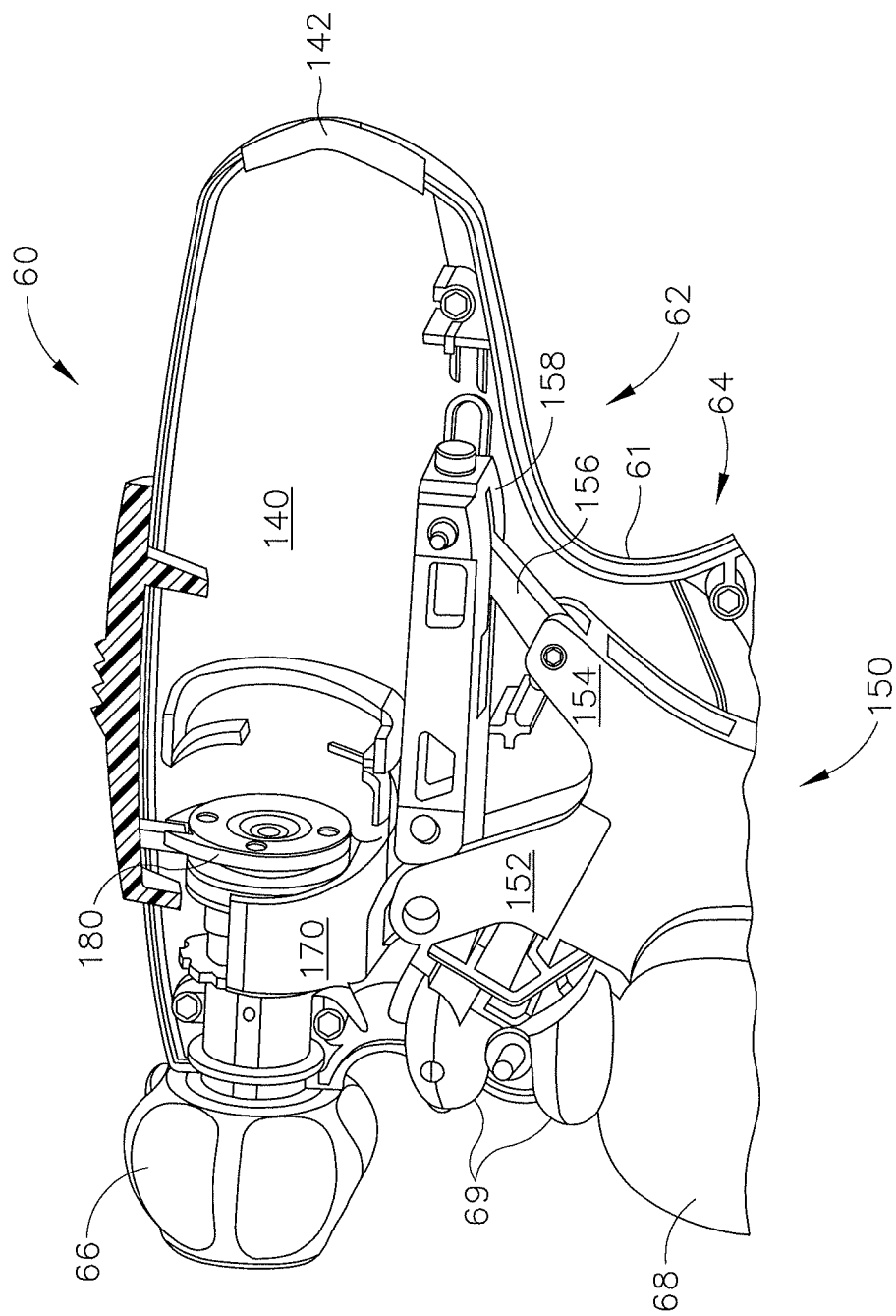
FIG. 2 depicts a partial side elevation view of an exemplary surgical instrument with a portion of a cover removed to show the interior of a mating housing portion of an exemplary multi-piece handle assembly.

FIG. 2 shows a partial side view of multi-piece handle assembly (60) with a portion of a cover (61) removed to show the internal components contained within mating housing portion (62) and a section of lower portion (64). As described above, lower portion (64) includes a pivotable trigger (68) and, optionally, a pair of toggle buttons (69). Trigger (68) of the present example is pivotable from a distal, open position to a proximal, closed position. A trigger assembly (150) is coupled to trigger (68) and is pivotally supported within multi-piece handle assembly (60). Trigger assembly (150) of the present example comprises a pivotable attachment arm (152) that may be pivoted about a pin (not shown), a trigger arm (154), an intermediate link (156), and an actuation arm (158). Actuation arm (158) is coupled to a trigger yoke (170) at the distal end of actuation arm (158). Actuation arm (158) comprises one or more mounting pins (not shown) extending outwardly from actuation arm (158). The mounting pins are sized to be slidably received in a corresponding elongated channel formed in cover (61). Accordingly, when trigger (68) is pivoted proximally from the open position to the closed position, attachment arm (152) and trigger arm (154) pivot within multi-piece handle assembly (60). Intermediate link (156) coupled to trigger arm (154) transfers this pivoting motion from trigger arm (154) to actuation arm (158) to slidably translate actuation arm (158) proximally via mounting pins within the elongated channel. Trigger yoke (170), which is coupled to actuation arm (158), is translated proximally as well. In one configuration, trigger yoke (170) is coupled to a force-limiting mechanism (180) that is coupled to transmission assembly (70), as will be described in more detail below, to operate an inner tubular actuating member. A cavity (140), shown in FIG. 2, is configured to receive transducer (100) therein from a transducer aperture (142) formed in cover (61). Cavity (140) is configured to receive at least a portion of transducer (100) therein such that transducer (100) and transmission assembly (70) may be coupled together. Still other configurations for multi-piece handle assembly (60) will be apparent to one of ordinary skill in the art in view of the teachings herein.

B. Exemplary Transducer

Figure 3:
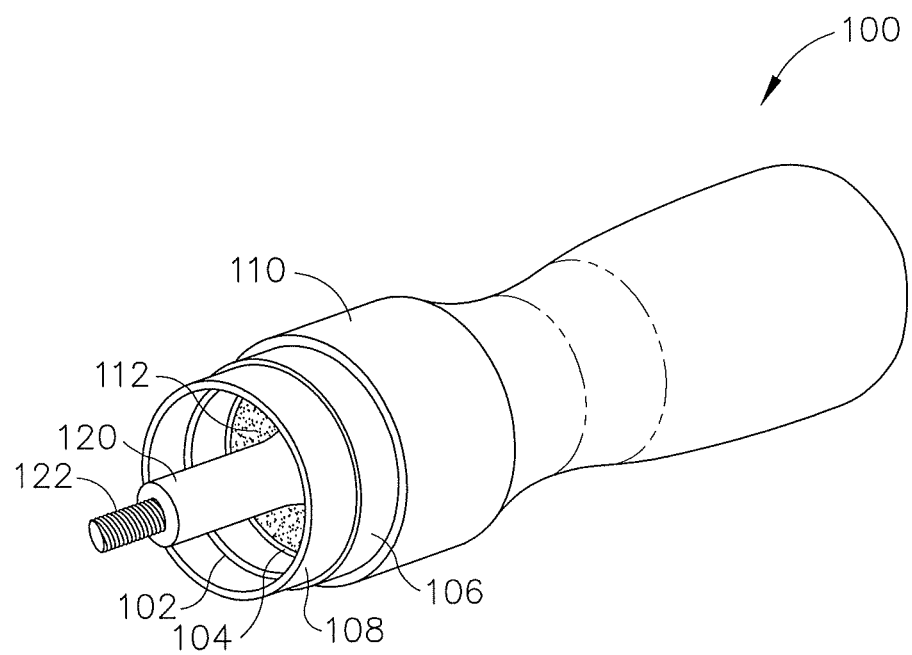
FIG. 3 depicts a perspective view of an exemplary transducer.

As shown in FIG. 3, transducer (100) of the present example is a tubular component that is coupled to generator (20) via cable (30), though it should be understood that transducer (100) may be a cordless transducer. In FIG. 3, transducer (100) is shown in body (110). Focusing on the distal end of transducer (100), transducer (100) includes a first conductive ring (102) and a second conductive ring (104) which are disposed within a body (110) of transducer (100). In one configuration, first conductive ring (102) comprises a ring member that is disposed between body (110) and a horn (120) extending distally from body (110). Horn (120) comprises distal horn threads (122) such that horn (120) is coupleable to waveguide (76), as will be discussed below in reference to FIG. 5. First conductive ring (102) is formed adjacent to, or as part of a flange (106) within a transducer cavity (108) such that first conductive ring (102) is electrically isolated from second conductive ring (104) and other conductive components of transducer (100). First conductive ring (102) is located on a non-conductive platform extending distally from body (110). First conductive ring (102) is electrically coupled to cable (30), shown in FIG. 1, by one or more electrical wires or conductive etchings (not shown) within body (110).

Second conductive ring (104) of transducer (100) similarly comprises a ring member that is disposed between body (110) and horn (120). Second conductive ring (104) is disposed between first conductive ring (102) and horn (120). As is shown in FIG. 3, first and second conductive rings (102, 104) are concentric members. Second conductive ring (104) is likewise electrically isolated from first conductive ring (104) and other conductive components of transducer (100). Similar to first conductive ring (102), second conductive ring (104) extends from the non-conductive platform. One or more washer-shaped spacers (112) may be disposed between first and second conductive rings (102, 104) or between the rings (102, 104) and other members of transducer (100). Second conductive ring (104) is also electrically coupled to cable (30), shown in FIG. 1, one or more electrical wires or conductive etchings (not shown) within body (110). One merely exemplary suitable ultrasonic transducer (100) is Model No. HP054, sold by Ethicon Endo-Surgery, Inc. of Cincinnati, Ohio.

As shown in the present example, the distal end of transducer (100) threadably couples to the proximal end of transmission assembly (70) via horn (120). The distal end of transducer (100) also interfaces with one or more electrical connections (not shown) via first and second conductive rings (102, 104) to electrically couple transducer (100) to toggle buttons (69) to provide a user with finger-activated controls for activating transducer (100) while using surgical instrument (50). Still other configurations for transducer (100) will be apparent to one of ordinary skill in the art in view of the teachings herein. For instance, first and second conductive rings (102, 104) may be omitted from the distal end of transducer (100) and the electrical coupling of transducer (100) to toggle buttons (69) may be accomplished by alternative methods, such as conductors at the proximal end of transducer (100), conductors located along the side of body (110) of transducer (100), directly from cable (30) and/or any other method as will be apparent to one of ordinary skill in the art in view of the teachings herein.

Figure 4:
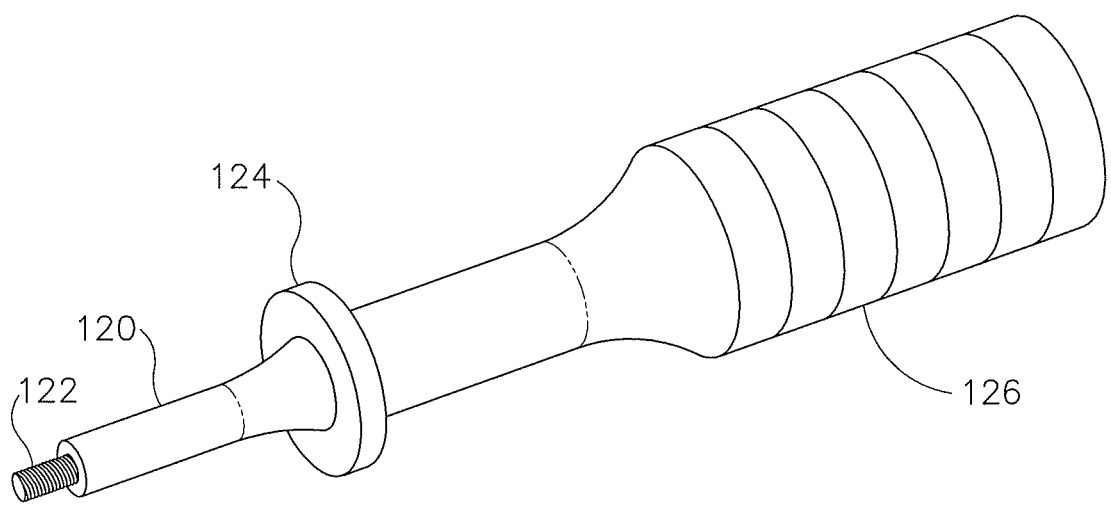
FIG. 4 depicts a perspective view of the transducer in FIG. 3 with a transducer body removed.

FIG. 4 depicts transducer (100) with body (110) removed. Mounting flange (124) near the distal end of transducer (100) and piezoelectric stack (126) at the proximal end of transducer (100) can be viewed with body (110) removed. When transducer (100) of the present example is activated via a toggle button (69), an electric field is created in piezoelectric stack (126) and horn (120) oscillates within and relative to body (110). Mounting flange (124) is used to couple horn (120) to body (110), to thereby support piezoelectric stack (126) in body (110). Transducer (100) is operable to create mechanical energy, or vibrations, at an ultrasonic frequency (such as 55.5 kHz). If transducer (100) is coupled to transmission assembly (70) via horn (120), then these mechanical oscillations are transmitted through waveguide (76) to end effector (80). In the present example, blade (82), being coupled to waveguide (76), oscillates at the ultrasonic frequency. Thus, when tissue is secured between blade (82) and clamp arm (84), the ultrasonic oscillation of blade (82) may sever and cauterize the tissue. An electrical current may also be provided through blade (82) and clamp arm (84) to cauterize the tissue. While some configurations for transducer (100) have been described, still other suitable configurations for transducer (100) will be apparent to one of ordinary skill in the art in view of the teachings herein.

C. Exemplary Transmission Assembly for Threaded Attachment

As noted previously, in some instances it may be useful to detach transmission assembly (70) from multi-piece handle assembly (60) and transducer (100). Merely exemplary instances include the use of multi-piece handle assembly (60) with multiple transmission assemblies (70) having different sized and/or shaped blades (82), use with various end effectors (80) with entirely different functions (e.g., RF end effectors, stapling end effectors, cutting end effectors, and/or etc.), or for reuse of a single multi-piece handle assembly (60) for multiple operations by a user. Accordingly, a configuration permitting the user to swap transmission assemblies (70) with multi-piece handle assembly (60) may be useful.

Figure 5:
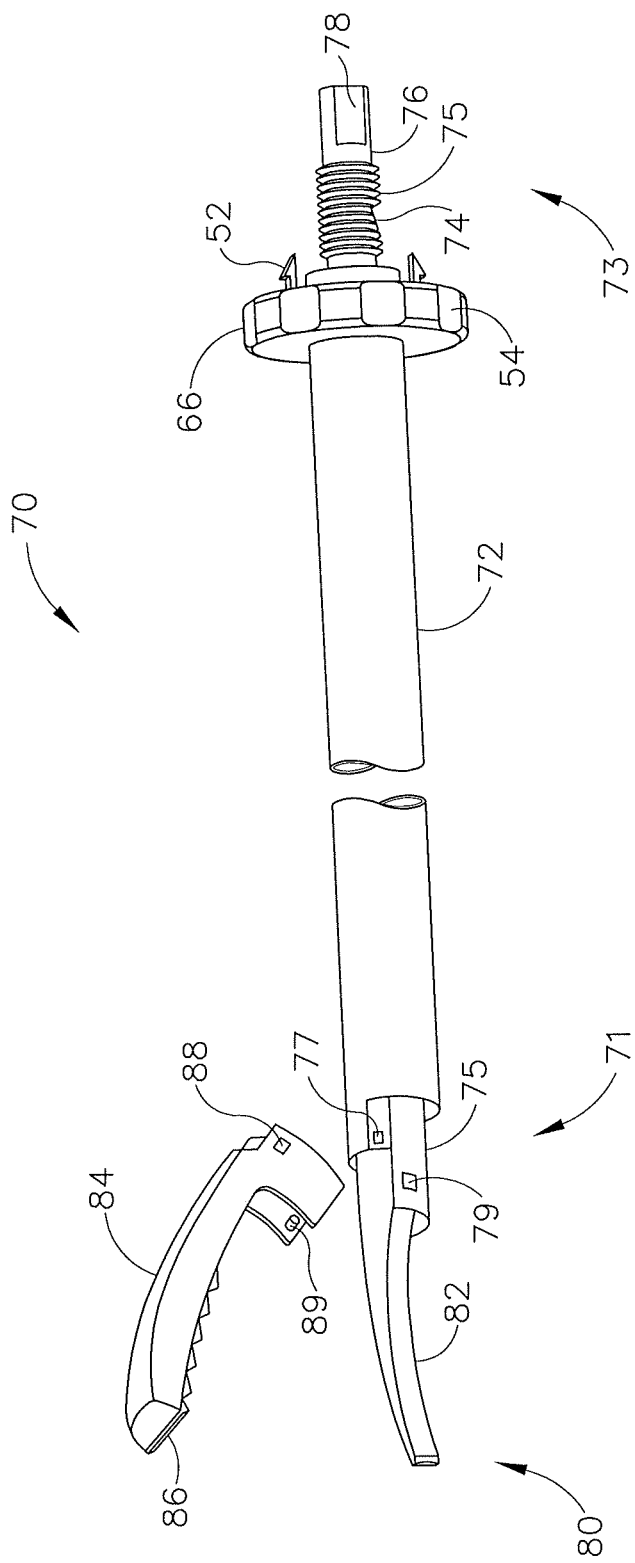
FIG. 5 depicts a perspective view of an exemplary transmission assembly.

One merely exemplary transmission assembly (70) is shown in FIG. 5 having a proximal end (73), a distal end (71), a wave guide (76), an inner tubular actuating member (75), an outer sheath (72), and an end effector (80) at the distal end of transmission assembly (70). In the present example, waveguide (76), inner tubular actuating member (75), and outer sheath (72) are coaxial members with waveguide (76) in the center, inner actuating member (75) disposed about waveguide (76), and outer sheath (72) disposed about inner actuating member (72).

Referring to distal end (71) of transmission assembly (70) first, end effector (80) comprises a blade (82), a clamp arm (84), and one or more optional clamp pads (86). In the present example, blade (82) is coupled to waveguide (76) such that the mechanical vibrations transmitted to waveguide (76) from transducer (100) are also transmitted to blade (82). Merely exemplary couplings for blade (82) to waveguide (76) include welding blade (82) to waveguide (76), integrally forming blade (82) with waveguide (76), mechanically or chemically coupling blade (82) to waveguide (76), and/or any other suitable configuration as will be apparent to one of ordinary skill in the art in view of the teachings herein. In one configuration blade (82) is a curved blade, such as blade (82) shown in FIG. 5, and in another configuration blade (82) may be a straight blade. Furthermore, blade (82) may have a variety of shapes and sizes. In the present example, blade (82) is a tapered rectangular blade, though it should be understood that blade (82) may include cylindrical, triangular, hemi-cylindrical, square, hooked, and/or any other shape for blade (82). Furthermore, additional features may be added to blade (82), including spherical tips, hooked tips, square tips, serrated edging, and/or any other additional features. Still other configurations for blade (82) will be apparent to those of ordinary skill in the art in view of the teachings herein.

Clamp arm (84) of the present example is a curved member that corresponds to the curvature of blade (82). Clamp arm (84) may optionally include clamp pads (86) to grip or secure tissue against blade (82). Such clamp pads may be configured in accordance with at least some of the teachings of U.S. Pat. Pub. No. 2006/0079874, entitled "Tissue Pad Use with an Ultrasonic Surgical Instrument," published Apr. 13, 2006, the disclosure of which is incorporated by reference herein. Pivotal movement of clamp arm (84) with respect to blade (82) is accomplished by a first pair of pivot points (88) on clamp arm (84) that pivotally couple to outer sheath (72) and a second set of pivot points (89) on clamp arm (84) that pivotally couple to inner tubular actuating member (75). In one merely exemplary configuration, outer sheath (72) is coupleable to multi-piece handle assembly (60) through a rotation knob (66), as will be described in greater detail below. First set of pivot points (88) of clamp arm (84) are pivotally connected to outer sheath (72) via corresponding through holes (77) on outer sheath (72). In one configuration, first set of pivot points (88) comprise through holes and a securing pin or rivet may be inserted through first set of pivot points (88) and through through holes (77) to secure clamp arm (84) to outer sheath (72). The pin in this configuration may be laser welded to clamp arm (84) or the pin may be laser welded to outer sheath (72). Of course through holes (77) may instead be outwardly extending pins and first set of pivot points (88) may be through holes. Still other configurations for first set of pivot points (88) and through holes (77) will be apparent to one of ordinary skill in the art in view of the teachings herein.

Second set of pivot points (89) of clamp arm (84) are pivotally connected to inner tubular actuating member (75) via corresponding through holes (79) on inner tubular actuating member (75). In one configuration, second set of pivot points (89) comprise through holes and a securing pin or rivet may be inserted through second set of pivot points (89) and through through holes (79) to secure clamp arm (84) to inner tubular actuating member (75). The pin in this configuration may be laser welded to clamp arm (84) or the pin may be laser welded to inner tubular actuating member (75). Of course through holes (79) may instead be outwardly extending pins and second set of pivot points (89) may be through holes. Still other pivotable configurations for second set of pivot points (89) and through holes (79) will be apparent to one of ordinary skill it the art in view of the teachings herein.

With clamp arm (84) so secured to outer sheath (72) and inner tubular actuating member (75), clamp arm (84) is pivotable when inner tubular actuating member (75) translates longitudinally. In the present configuration, inner tubular actuating member (75) is translatable relative to the longitudinal axis of outer sheath (72) and is coupled to force-limiting mechanism (180) within multi-piece handle assembly (60). Thus, when force-limiting mechanism (180) translates via trigger (68) and trigger assembly (150), clamp arm (84) is pivotable from an open position to a closed position.

Referring now to proximal end (73) of transmission assembly (70), a rotation knob (66) couples outer sheath (72) to multi-piece handle assembly (60). In the present example, rotation knob (66) comprises an inner ring portion (not shown) having one or more connectors (52) extending proximally therefrom, an outer ring (54), and a pin (not shown) extending through outer ring (54), outer sheath (72), inner tubular actuating member (75), and waveguide (76). Accordingly, when outer ring (54) of rotation knob (66) is rotated, waveguide (76), inner tubular actuating member (75), and outer sheath (72) also rotate. Inner ring portion and outer ring (54) of the present example are complementary bearing components such that outer ring 254) is rotatable relative to inner ring portion. It should be understood that the pin does not extend though inner ring portion. As previously noted, inner ring portion includes connectors (52). In the present example connectors (52) are shown as snap-fit connectors, though other suitable connecting features, such as threading, adhesives, pins, clips, snaps, and/or other connectors may be used as will be apparent to one of ordinary skill in the art in view of the teachings herein. When transmission assembly (70) is assembled with multi-piece handle assembly (60) and transducer (100), as will be discussed below, connectors (52) of the present example insert into one or more recesses (not shown) and couple rotation knob (66) to cover (61) of multi-piece handle assembly (60). A release mechanism, such as a push button (not shown) on multi-piece handle assembly (60) or on rotation knob (66) may be provided to decouple connectors (52) from cover (61) when transmission assembly (70) is to be removed. Alternatively, connectors (52) may be designed to break-away when transmission assembly (70) is decoupled. Further still, if threading is used, inner portion of rotation knob (66) may be rotated to decouple from multi-piece handle assembly (60). Still other suitable configurations for rotation knob (66) will be apparent to one of ordinary skill in the art in view of the teachings herein.

Still referring to proximal end (73) of transmission assembly (70), external threads (74) are included at the proximal end of inner tubular actuating member (75) as shown in FIG. 5. External threads (74) screw into complementary threads (not shown) of a threaded member (not shown), but other configurations for external threads (74) will be discussed in further detail below. Additionally, a recess having internal threading (78) is included at the proximal end of waveguide (76) as shown in FIG. 5. Internal threading (788) screws onto horn threads (122) to couple waveguide (76) to transducer (100). Of course other suitable configurations for transmission assembly (70) will be apparent to one or ordinary skill in the art in view of the teachings herein.

III. Exemplary Surgical Instrument with Detachable Transmission Assembly

As noted above, transmission assembly (70) may be provided as a disposable assembly, thereby allowing surgical instrument (50) to be used many times by replacing transmission assembly (70) between uses. In addition or in the alternative, it may be simply desirable to keep transmission assembly (70) separate from surgical instrument (50) when surgical instrument (50) is not in use such that surgical instrument (50) and transmission assembly (70) may be stored separately. Furthermore, a user may wish to select from different transmission assemblies (70) having different features, configurations, and/or operabilities depending on the particular context. Transmission assemblies (70) may be attached to handle assembly (60) by various features either in handle assembly (60) or on transmission assemblies (70). Various features to attach different transmission assemblies (70) are discussed in more detail below. Transmission assemblies (70) may be attached or detached at proximal end (73) such that the entire transmission assembly (70) is disposable. Transmission assemblies (70) may also be attached or detached at distal end (71) such that end effector (80) is disposable. Various types of transmission assemblies and end effectors may thus be attached to a handle assembly. Other suitable configurations for attaching transmission assemblies (70) will be apparent to one with ordinary skill in the art based on the teachings herein.

A. Exemplary Attachment Device in Handle Assembly

Figure 6:
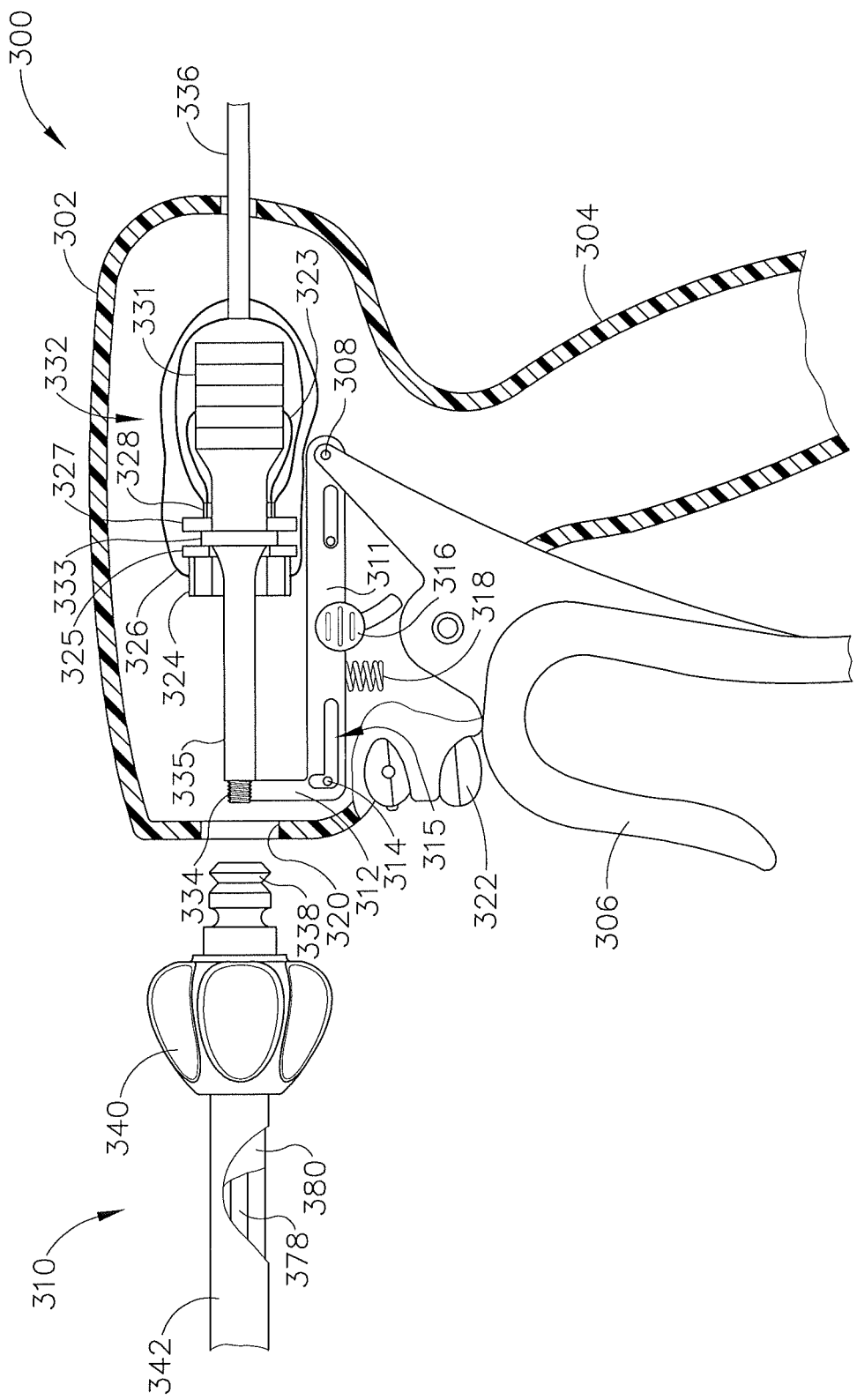
FIG. 6 depicts a partial side view of an exemplary surgical instrument with a portion of a cover removed.
Figure 7:
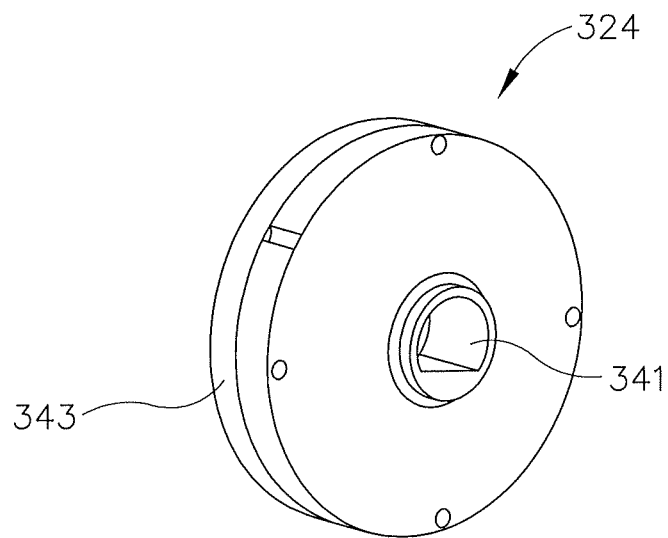
FIG. 7 depicts a perspective view of the motor in FIG. 6.

FIG. 6 shows a cross sectional view of a surgical instrument (300) with a detachable transmission assembly (310). Surgical instrument (300) is an exemplary variation of surgical instrument (50), described above. Surgical instrument (300) of this example comprises a handle assembly (302) having handle portion (304) shaped like a pistol grip such that a user and/or clinician may use surgical instrument (300) with a single hand thereby freeing the other hand. Handle portion (304) may alternatively have a scissor grip shape, pencil grip shape, and/or any other suitable shape. A connector opening (320) is formed on the distal end of handle assembly (302) and will be described in further detail below. A portion of a pivoting trigger (306) extends outside of handle assembly (302) and may be actuated by a user. Trigger (306), as seen in FIG. 6 extends into handle assembly (302) and terminates at a proximal pivot (308) where trigger (306) connects to yoke (312) via a yoke arm (311).

Yoke (312) comprises a release switch (316), and is configured to selectively engage transmission assembly (310) as will be described in greater detail below. A spring (318) is also connected to yoke (312). Spring (318) is positioned to provide an upward bias against yoke (312). Release switch (316) in the present example extends transverse to yoke (312) and further extends through handle assembly (302) to the outside of handle assembly (302) such that a user may actuate release switch (316) to pivot yoke (312) downwardly. Furthermore, at least one toggle button (322) is embedded into handle assembly (302). Toggle button (322) may be manipulated by the user to control some of the operations of surgical instrument (300) as will be described below. In the present example, toggle button (322) is positioned sufficiently close enough to trigger (306) and handle portion (304) such that toggle button (322) may be actuated without significantly shifting the hand of the user. However, other suitable positions for toggle button (322) may be used as would be apparent to one of ordinary skill in the art in view of the teachings herein.

A motor (324) is positioned within handle assembly (302) near the distal end of transducer (100). Motor (324) is in communication with a cable (336) through wires (326). In addition or in the alternative, motor (324) may be in communication with a logic controller and/or generator board. Cable (336) is operable to power motor (324) in the present example through wires (326). Motor (324) is operable to turn in both clockwise and counter clockwise directions. Motor (324) is further in communication with a transducer (332). Motor (324) of the present example comprises a pancake motor such that motor (324) includes a rotor (341) defining inner diameter and a stator (343) defining outer diameter such that inner diameter rotates when motor (324) is activated, while outer diameter is stationary when motor (324) is activated. Motor (324) may be positioned with the inner diameter about transducer (332). In the present example, motor (324) is positioned about horn (335). Motor (324) may also be positioned about piezoelectric stack (331) or at any other suitable position. As shown in FIG. 6, when motor (324) is activated, piezoelectric stack (331), horn (335), and threads (334) will rotate within handle assembly (302).

Figure 8:
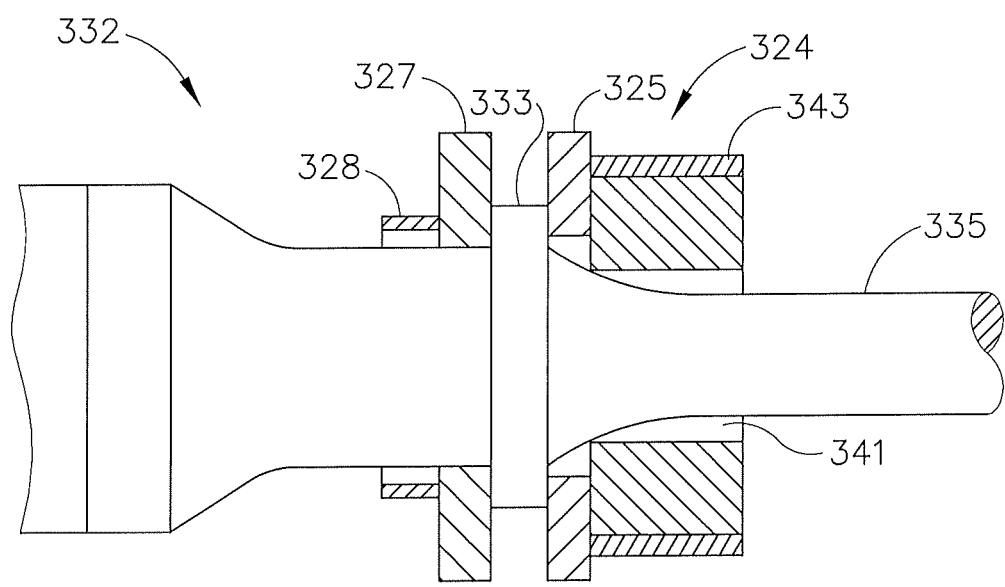
FIG. 8 depicts a cross section view of a portion of the transducer and compression plates in FIG. 6.

Because of the oscillating movement of transducer (332), it may be beneficial to dampen transducer (332) relative to motor (324). Dampening transducer (332) may be performed by using compression plates (325, 327) secured to mounting flange (333) of transducer (332). Various sizes and amounts of compression plates may be used to dampen transducer (332) to a desired oscillating movement. One of the compression plates (325, 327) may be embedded with motor assembly (324). FIG. 8 depicts a cross section of horn (335) with compression plates (325, 327) positioned about mounting flange (333) with motor (324). Compression plates (325,327) are positioned about the outer diameter of horn (335). The inside diameter of motor (324) is positioned about the horn (335) and adjacent to the distal face of compression plate (325) in the present example. Motor (324), compression plates (325, 327), and piezoelectric stack (331) are coaxially aligned and coupled together with flange (333). Rotor (341) of motor (324) may be attached by welding, epoxy, or other suitable means. Stator (343) of motor is secured to handle assembly (302), such that motor (324) supports transducer (332) within handle assembly (302). When motor (324) is activated, the rotor (341) of motor (324) will rotate, thus rotating compression plates (325, 327), piezoelectric stack (331), horn (335), and threading (334). Slip ring (328) may be provided adjacent to the proximal face of compression plate (327), thereby permitting transducer (332) to rotate freely in relation to cable (336) while maintaining electrical continuity between cable (336) and transducer (332). Slip ring (328) may provide slipping electrical contacts for communication with cable (336) using various components and features as will be apparent to those of ordinary skill in the art in view of the teachings herein. Slip ring (328) may be connected to piezoelectric stack (331) by wires (323) to activate piezoelectric stack (331). As will be discussed below, motor (324) is used to couple transmission assembly (310) to transducer (332).

As seen in the illustrated version, transducer (332) is positioned within handle assembly (302). The distal end of transducer (332) defines distal horn threads (334) and the proximal end of transducer (332) leads to a cable (336). Cable (336) leads out of handle assembly (302) and leads to, for example, a generator (20) as depicted in FIG. 1. Thus, electrical power from generator (20) may be transmitted through cable (336) to transducer (332), which then converts the electrical power into ultrasonic vibrations, which are further communicated to distal horn threads (334).

Transmission assembly (310) includes a sheath (342), an inner actuating member (380), a waveguide (378), and an end effector (not shown). These components are all coaxially aligned, with inner actuating member (380) being positioned within sheath (342); and waveguide (378) being positioned within inner actuating member (380). In the present example, these components are also substantially analogous to sheath (342), inner actuating member (220), waveguide (210), and end effector (204) described above, respectively. Proximal end of inner actuating member (380) has an engagement recess (339). Engagement recess (339) is received in yoke (312), such that translation of yoke (312) provides translation of inner actuating member (380). Yoke (312) is translated by pivoting trigger (306) toward and away from grip (304). Thus, inner actuating member (380) may be reciprocated relative to sheath (342) in order to selectively pivot a clamp member at the distal end of transmission assembly (310).

In addition, waveguide (378) has a proximal end (not shown) that is slidably disposed interiorly relative to proximal end (382) of inner actuating member (380). The proximal end of waveguide (378) includes an integral engagement flange (338) and defines internal threads complementary to distal horn threads (334). Thus, when the internal threads of waveguide (378) initially engage distal horn threads (334), motor (324) may be activated to rotate transducer (332) and distal horn threads (334), to thereby mechanically and acoustically couple transducer (372) to waveguide (378). Motor (324) may also be activated to rotate transducer (332) and distal horn threads (334) in the opposite direction to decouple distal horn threads (334) from waveguide (378).

One or more sensors may be used to monitor the amount of torque present at the coupling of waveguide (378) and distal horn threads (334), and such information may be used to automatically stop motor (324) when the appropriate level of torque is reached. An appropriate level of torque may be selected to provide an ideal mechanical and acoustic coupling between waveguide (378) and transducer (332), as will be apparent to those of ordinary skill in the art in view of the teachings herein. By way of example only, the torque may be sensed by monitoring the back electromotive force of motor (324). Still other suitable components and techniques that may be used to sense the appropriate level of torque, as well as ways in which torque information may be used to stop motor (324) at the appropriate time, will be apparent to those of ordinary skill in the art in view of the teachings herein. By way of example only, a mechanical torque limiting device may be used. In addition or in the alternative, motor (324) may simply be set to rotate a prescribed number of times, with rotations being tracked by an encoder assembly, etc. It will also be appreciated that other types of end effectors (80) may be used with surgical device (300) as would be apparent to one of ordinary skill in the art in view of the teachings herein.\

B. Exemplary Attachment Detection Device

FIGS. 9A and 9B show an exemplary attachment detection device (600) to couple a transmission assembly (680) to a handle assembly (400). Transmission assembly (680) and handle assembly (400) are similar to the ones described above. When handle assembly (400) is properly attached to transmission assembly (680), detection device (600) signals a user of such attachment. Detection device (600) includes cartridge (601), battery (602), microprocessor (604), resilient member (606), piezoelectric transducer (608), and contact bushing (610). Cartridge (601) is configured to enclose a transmission assembly (680) within an opening such that the proximal end of transmission assembly (680) is even with the proximal end of cartridge (601) or fully within cartridge (601). Battery (602) is located within cartridge (601) and is configured to provide power to microprocessor (604) via wires (626). Microprocessor (604) is located within cartridge (601) and communicates with a sensor (616) and piezoelectric transducer (608) via wires (626).

Sensor (616) is operable to detect engagement between handle assembly (400) and transmission assembly (680). For instance, sensor (616) could be configured to detect movement of contact bushing (610), which would enable sensor (616) to detect distal force against transmission assembly (680) when transducer assembly (100) is pushed against transmission assembly (680). As another merely illustrative example, sensor (616) may comprise a ring sensor that measures torsional stress. In some versions, such a sensor (616) is formed by a piezoelectric film that is fixed between a flange of transmission assembly (680) and the housing of cartridge (601). As torsional strain is applied, the film is deformed and generates a voltage. As another merely illustrative example, sensor (616) may be formed by two coils with a high mutual inductance, with one coil on one side of an elastomeric joint and another coil on the other side of the elastomeric joint. Small changes in relative position or orientation may result in large changes in mutual inductance. In some versions, such changes in mutual inductance may be measured as changes in resonance when the coils are coupled in a resonant circuit. As yet another merely illustrative example, sensor (616) may be formed by a laser diode on a flange of transmission assembly (680) or elsewhere, with sensor (616) being fixed to the housing of cartridge (601) and being configured to detect deflection of the flange orientation relative to the housing by sensing deflection of the light emitted from the laser diode. Other suitable ways in which sensor (616) may be configured will be apparent to those of ordinary skill in the art in view of the teachings herein. When sensor (616) detects handle assembly (400) at the proximal opening of cartridge (601), microprocessor (604) activates piezoelectric transducer (608) through wires (626). Microprocessor (604) may also activate piezoelectric transducer (608) manually by a user (e.g. in response to a manually operated switch or button, etc.) when handle assembly (400) is inserted into the proximal opening of cartridge (601). Microprocessor (604) activates piezoelectric transducer (608) by sending an electric signal to convert to mechanical motion.

As piezoelectric transducer (608) oscillates, resilient member (606) is in contact with piezoelectric transducer (608), providing dampening of piezoelectric transducer (608) relative to other components of cartridge (601). In the present example, resilient member (606) is located distally to piezoelectric transducer (608). Resilient member (606) can be a spring or any other suitable resilient member. Contact bushing (610) is in contact with piezoelectric transducer (608), such that contact bushing (610) oscillates with piezoelectric transducer (608). Contact bushing (610) of the present example is made of a metal material, though it should be understood that any other suitable material(s) may be used. Contact busing (610) is in contact with the distal end of transmission assembly (680).

As described above, handle assembly (400) contains transducer horn (120) with external threads (122). Threads (122) of horn (120) may be attached to corresponding internal threads (74) at the proximal end of waveguide (78). Transducer assembly (100) may be held within handpiece (402). To attach handle assembly (400) to transmission assembly (680), a portion of handle assembly (400) is placed though the proximal opening of cartridge (601). Then the user grasps cartridge (601) and rotates cartridge (601) relative to handle assembly (400), thereby threadably securing internal threads (74) of transmission assembly (680) with threads (122) of horn (120).

When handle assembly (400) enters the proximal opening of cartridge (601) a sensor (not shown) in cartridge (601) detects handle assembly (400). Suitable types of sensors will be apparent to one with ordinary skill in the art in view of the teachings herein. For instance, insertion of handle assembly (400) into cartridge (601) may push transmission assembly (680) distally, which may cause contact bushing (610) to move distally. Sensor (616) may detect this distal movement of contact bushing (610), thereby detecting insertion of handle assembly (400) into cartridge (601). When handle assembly (400) is detected in cartridge (601), microprocessor (604) activates piezoelectric transducer (608). An electric signal sent by microprocessor (604) is converted to mechanical oscillations by piezoelectric transducer (608). These oscillations send a waveform through transmission assembly (680) via contact bushing (610). The waveform returns back to contact bushing (610) and is picked up by sensor (616). Microprocessor (604) is configured to track the transmission and return times to calculate the total travel time for the waveform. These oscillations continue as the user rotates cartridge (601) relative to handle assembly (400) to secure transmission assembly (680) to handle assembly (400). When transmission assembly (680) is not in contact with handle assembly (400), the total travel time for the waveform through transmission assembly (680) will be short. When transmission assembly (680) is fully and properly attached to handle assembly (400), a longer waveform will oscillate and return to contact bushing (610) in a known amount of time. Upon detecting a resonant state, microprocessor (604) signals to a built in user indicator that transmission assembly (680) is now appropriately secured to transducer (100).

Microprocessor may be configured to activate speaker (612), LED (614) and/or other indicator to show that transducer (100) is properly attached to transmission assembly (680). In the present example, a speaker (612) is located at the distal end of cartridge (601). Speaker (612) may provide a user with an audible signal when transducer (100) and transmission assembly (680) are attached. An LED (614) or other light source may be on cartridge (601) to visibly indicate to a user that transducer (100) and transmission assembly (680) are attached. Speaker (612) and LED (614) may be at various locations on cartridge (601) capable of signaling to a user. Other suitable indication methods will be apparent to one with ordinary skill in the art based on the teachings herein. Once the user receives the indication that transmission assembly (680) is properly coupled with transducer (100), the user may stop rotating cartridge (601) relative to handle assembly (400). The user may then pull cartridge (601) away from transmission assembly (680), which slides out of cartridge (601) and remains properly secured to transducer (100).

Cartridge (601) may also be configured to attach an end effector assembly to a transmission assembly. An end effector assembly may be enclosed within cartridge so that a sensor detects when a transmission assembly enters the proximal opening of cartridge (601). Piezoelectric transducer (608) and resilient member (606) may then send a waveform through end effector assembly. Once transmission assembly and end effector assembly are properly connected, a known a waveform will be detected. A user may then be alerted that end effector assembly and transmission assembly are properly attached. Still other variations will be apparent to one with ordinary skill in the art in view of the teachings herein.

C. Exemplary Torque Attachment Device

FIGS. 10A and 10B depict an exemplary torque attachment device (700). Torque attachment device (700) does not allow a user to remove transmission assembly (780) from cartridge (701) until a correct amount of torque has been applied to properly attach a transmission assembly (780) to a transducer assembly (832). Transmission assembly (780) is similar to the transmission assemblies described above, except that transmission assembly (780) also has a transmission assembly collar (730) and a lock button (732), as better seen in FIG. 11. Transmission assembly collar (730) is attached over the proximal end of transmission assembly (780). Lock button (732) is on the proximal end of transmission assembly collar (730). Lock button (732) is capable of flexing downward onto horn (820) within handle assembly (800). Handle assembly (800) is similar to the above handle assemblies, except that horn (820) of the transducer assembly (832) within handle assembly (800) has a keyed portion (824). When lock button (732) is flexed downward, it corresponds to keyed portion (824). Keyed portion (824) may be a flat surface, or any other suitable shape operable to prevent transducer assembly (832) from rotating within handle assembly (800) when lock button (732) is depressed into keyed portion (824). The distal portion of handle assembly (800) may be contained in handle cartridge (801). Handle cartridge (801) is configured to securely hold handle assembly (800). Handle cartridge (801) may be sized to hold the entire handle assembly (800) or merely a portion of the distal end of handle assembly (800). When handle cartridge (801) is urged into engagement with torque attachment device (700), handle cartridge (801) deflects lock button (732) into keyed portion (824) to prevent rotation of horn (820) relative to handle cartridge (801).

Torque attachment device (700) includes an external cartridge (701), an internal cartridge (702), a torque collar (720), and a torque limiting sleeve (710). External cartridge (701) is configured to contain transmission assembly (780) so that transmission assembly (780) is fully enclosed in external cartridge (701). Internal cartridge (702) lies within external cartridge (701). Internal cartridge (702) is operable to hold and align transmission assembly (780). Internal cartridge (702) may extend the entire length of external cartridge (701) or internal cartridge (702) may have a smaller length. Internal cartridge (702) is also flexible and capable of bending inward. Moreover, external cartridge (701) and internal cartridge (702) may be configured as a single piece.

Torque collar (720) is located within external cartridge (701). Torque collar (720) may be positioned around internal cartridge (702), transmission assembly collar (730), or transmission assembly (780). As shown in FIG. 12, torque collar (720) includes a drive ring (722) positioned around internal cartridge (702), which is positioned around transmission assembly (780). Drive ring (722), internal cartridge (702), and transmission assembly (780) are coaxially aligned. When a user rotates external cartridge (701), this rotation is communicated to the outside of torque collar (720). Drive ring (722) is resiliently biased to press against internal cartridge (702), which is resiliently biased to press against transmission assembly (780). Accordingly, as a user rotates torque attachment device (700), the force applied to transmission assembly (780) causes transmission assembly (780) to rotate simultaneously with torque attachment device (700).

Torque collar (720) includes an internal protrusion (726) at one end of drive ring (722). When drive ring (722) is resiliently biased to press against internal cartridge (702), protrusion (726) is resiliently biased below the opposite end of drive ring (722) to contact an end surface of internal cartridge (702), as shown in FIG. 12. The resilient bias of protrusion (726) operates to allow a user to rotate transmission assembly (780) in only one direction. In the present example, protrusion (726) is resiliently biased downward to push against an end surface of internal cartridge (702) in a clockwise direction, thereby to allow a user to rotate transmission assembly (780)

in a counterclockwise direction. If a user rotated torque collar (720) in a counterclockwise direction in the present example, protrusion (726) would not push against an end surface of internal cartridge (702) and thus would slide over and not rotate internal cartridge (702) or transmission assembly (780). The protrusion feature (726) of torque collar (720) therefore acts to only allow transmission assembly (780) to be rotated in one direction relative to handle assembly (800).

Torque attachment device (700) contains a space (704) between external cartridge (701) and transmission assembly (780). Handle cartridge (801) contains alignment feature (802) that corresponds to space (704). As handle cartridge (801) is slid into the proximal opening of torque attachment device (700), alignment feature (802) slides into space (704). Alignment feature (802) ensures that external threads (822) of horn (820) are aligned with the corresponding internal threads in transmission assembly (780). As handle cartridge (801) enters torque attachment device (700), lock button (732) is depressed by alignment feature (802) and the internal portion of handle cartridge (801). When lock button (732) is pressed down, it is depressed into keyed portion (824) on horn (820). Lock button thereby prevents horn (820) and external threads (822) from rotating. A user may now grip and rotate external cartridge (701) in a counterclockwise fashion to screw transmission assembly (780) onto handle assembly (800). As user grips external cartridge (701), drive ring (722) is resiliently biased onto internal cartridge (702), which is resiliently biased onto transmission assembly (780). The resilient biasing provides a force such that cartridge (701), drive ring (722), and transmission assembly (780) to rotate simultaneously. As transmission assembly (780) is rotated with cartridge (701), transmission assembly (780) is connecting with external threads (822) of transducer assembly (832).

A user may rotate external cartridge (701) until a proper amount of torque is reached to connect transmission assembly (780) and transducer assembly (800). A torque limiting sleeve (710) is contained within external cartridge (701). Torque limiting sleeve (710) is positioned between torque collar (720) and transmission assembly (780). Torque limiting sleeve (710) allows rotation of transmission assembly (780) until a sufficient amount of torque is reached. At that stage, torque limiting sleeve (710) then snaps and produces an audible signal, such as clicking. Upon further rotation, torque collar (720) springs open to release pressure from transmission assembly (780). Transmission assembly (780) can no longer rotate upon rotation of cartridge (701). As maximum torque is reached, release of extra torque also releases transmission assembly (780) from internal cartridge (702). A user may then remove torque attachment device (700) from transmission assembly (780). Until a sufficient amount of torque is reached, transmission assembly (780) cannot be removed from internal cartridge (702), such that internal cartridge (702) prevents the user from activating transmission assembly (780) until transmission assembly (780) is properly coupled with transducer assembly (832). As a user removes torque attachment device (700), lock button (732) is released from keyed portion (824) of horn (820). Horn (820) is now free for user to rotate relative to the handpiece (810) during the procedure.

To remove transmission assembly (780) from transducer assembly (832), user may depress lock button (732) into keyed portion (824) to lock transducer from rotating relative to the handpiece (810). User may then reverse rotate transmission assembly (780) and disengage it from handle assembly (800). The transmission assembly collar (730) and lock button (732) would remain coupled with handle assembly (800) while sleeve (734) and the blade of transmission assembly (780) would be removed.

Torque attachment device (700) may also be configured to attach an end effector assembly to a transmission assembly. An end effector assembly may be enclosed within cartridge (701) so that a torque collar (720) is positioned around an end effector assembly. As force is applied to rotate external cartridge (701), a force is applied torque collar (720) and an end effector assembly. Rotation of torque attachment device (700) may then attach an end effector assembly to a transmission assembly, located in handle cartridge (800). Still other variations will be apparent to one with ordinary skill in the art in view of the teachings herein.

D. Exemplary Motorized Torque Attachment Device

A torque attachment device (900) may also be motorized to attach a transmission assembly (980) to a transducer assembly (1032), as shown in FIGS. 13A-13B. Transmission assembly (980) is similar to transmission assemblies described above. Handle assembly (1000) is similar to handle assemblies described above, except that handle assembly (1000) of this example includes a micro linear motor (1004). Micro linear motor (1004) is operable to prevent rotation of horn (1020) and external threads (1022) relative to handpiece (1010). Micro linear motor (1004) may be configured to selectively engage lock block (1006) via shaft (1008). Lock block (1006) is unitarily secured to transducer assembly (1032), thus selectively preventing horn (1020) from rotating relative to handpiece (1010) when micro linear motor (1004) engages lock block (1006). The force applied by micro linear motor (1004) to lock block (1006) thereby prevents horn (1020) and external threads (1022) from rotating during the attachment of transmission assembly (980). Lock block (1006) may be mounted to mounting flange (1027), or another part of the transducer assembly (1032) as will be apparent to one with ordinary skill in the art in view of the teachings herein.

Motorized torque attachment device (900) is similar to torque attachment device (700), except that motorized torque attachment device further includes a battery (908), a motor (904), a slip clutch (906), and gears (910, 912). External cartridge (901) is configured to contain transmission assembly (980) so that transmission assembly (980) is fully enclosed in external cartridge (901). Internal cartridge (902) lies concentrically within external cartridge (901). Internal cartridge (902) is operable to hold and align transmission assembly (980). Internal cartridge (902) may extend the entire length of external cartridge (901) or internal cartridge (902) may have a smaller length. Internal cartridge (902) is connected to gear (912) at the distal end of internal cartridge (902). Internal cartridge (902) is configured to rotate relative to external cartridge (901) in response to rotation of gear (912).

Torque collar (720) is located within external cartridge (901). Torque collar (720) may be positioned around internal cartridge (902) or transmission assembly (980). As shown in FIG. 12, torque collar (720) includes a drive ring (722). In the present example, torque collar (720) is positioned around internal cartridge (902), which is positioned around transmission assembly (980). Drive ring (722), internal cartridge (902), and transmission assembly (980) are concentrically aligned. When motor (904) is activated to rotate internal cartridge (902), this rotation is communicated to torque collar (720). Drive ring (722) is resiliently biased to press against internal cartridge (901), which is resiliently biased to press against transmission assembly (980). Accordingly, as motor (904) rotates internal cartridge (902), the force applied to transmission assembly (980) causes transmission assembly (980) to rotate simultaneously with internal cartridge (902).

Torque collar (720) includes an internal protrusion (726) at one end of drive ring (722). Drive ring (722) is resiliently biased to press against internal cartridge (902), such that protrusion (726) is resiliently biased below the opposite end of drive ring (722) to contact an end surface of internal cartridge (902). The resiliently biasing of protrusion (726) operates to allow a motor (904) to rotate transmission assembly (780) in only one direction. In the present example, protrusion (726) is resiliently biased to contact internal cartridge (902) to allow a motor (904) to rotate transmission assembly (780) in a clockwise direction. If motor (904) were to rotate in the opposite direction, protrusion (726) would slip over internal cartridge (902) and transmission assembly (980), thereby preventing rotation of transmission assembly (780) in a counterclockwise direction.

As shown in FIGS. 13A-13B, the inner diameter of external cartridge (901) is sized to allow a portion of handpiece (1010) to fit within external cartridge (901). The proximal end of internal cartridge (902) of torque attachment device (900) is slightly contained within external cartridge (901) to allow a portion of handpiece to slide into external cartridge (901) and contact the proximal end of internal cartridge (902). The sizing of the inner diameter of external cartridge (901) and handpiece (1010) aligns external threads (1022) of horn (1020) to the internal threads on transmission assembly (980). As handle assembly (1000) is inserted into the proximal opening of torque attachment device (900), motor (904) may be activated. Motor (904) may be activated manually by a user, or automatically upon detection of handle assembly (1000) by a sensor (e.g. a load switch contacting the distal end of transmission assembly (980)). Suitable methods of activating motor (904) will be apparent to those with ordinary skill in the art in view of the teachings herein. Motor (904) is located in the distal portion of cartridge (901). Battery (908) is configured to power motor (904) through wires (926). Motor (904) is torque sensitive and is connected to slip clutch (906). Slip clutch (906) is configured to allow motor (904) to reach a sufficient amount of torque and then stall. As motor (904) is rotating before the sufficient amount of torque is reached, motor (904) rotates gears (910, 912), thereby rotating internal cartridge (902) and transmission assembly (980) relative to stationary handle assembly (1000).

Motor (904) may rotate until a proper amount of torque is reached to connect transmission assembly (980) and handle assembly (1000). Once a known amount of torque is reached, motor (904) will stall. After a short period of stall, motor (904) automatically reverses direction. Any suitable process or other control module may provide such a control algorithm. The reversed pressure and rotation on torque collar (720) allows torque collar (720) to slip about transmission assembly (980), enabling transmission assembly (980) to stay in place. Accordingly, as motor (904) reverses direction, transmission assembly (980) remains secured to transducer assembly (1032), while transmission assembly (980) is released from internal cartridge (902). A user may then remove torque attachment device (900) from transmission assembly (980). Until a sufficient amount of torque is reached, transmission assembly (980) cannot be removed from cartridge (901), such that cartridge (901) prevents the user from activating transmission assembly (980) until transmission assembly (980) is properly coupled with transducer assembly (1032).

As a user removes torque attachment device (900), linear motor (1004) releases lock block (1006). Transducer assembly (1032) is now free for user to rotate relative to handpiece (1010) during the procedure. To remove transmission assembly (980) from transducer assembly (1032), linear motor (1004) may again be activated to selectively engage lock block (1006) on mounting flange (1027) of the transducer to prevent horn (1020) from rotating relative to handpiece (1010). User may then reverse rotate transmission assembly (980) and disengage transmission assembly (980) from transducer assembly (1032).

Torque attachment device (900) may also be configured to attach an end effector assembly to a transmission assembly. An end effector assembly may be enclosed within cartridge (901) so that a torque collar (720) is positioned around an end effector assembly. Motor (904) may be activated to rotate internal cartridge (902) and an end effector assembly. Rotation of torque attachment device (900) may then attach an end effector assembly to a transmission assembly. Still other variations will be apparent to one with ordinary skill in the art in view of the teachings herein.

E. Exemplary Torque Attachment Detection Device

An end effector assembly (80) or transmission assembly (70, 310, 680, 780, 980) may be threaded to a transducer assembly (100, 332, 832, 1032) using a torque attachment device (600, 700, 900) described above; or a torque wrench described in U.S. Pat. Pub. No. 2008/0200940, entitled "Ultrasonic Device for Cutting and Coagulating," the reference of which is incorporated herein. As described above, a torque attachment device (600, 700, 900) or other suitable torque wrench may be used to attach an end effector assembly (80) or transmission assembly (70, 310, 680, 780, 980) to a transducer assembly (100, 332, 832, 1032). When transmission assembly (70, 310, 680, 780, 980) reaches a sufficient amount of torque to properly attach to transducer assembly (100, 332, 832, 1032), torque limiting sleeve (710) or other suitable device snaps to loosen the force applied to rotate transmission assembly (70, 310, 680, 780, 980). Accordingly, continuing to rotate a torque attachment device (600, 700, 900) will not rotate transmission assembly (70, 310, 680, 780, 980). Torque limiting sleeve (710) provides an audible click when torque limiting sleeve (710) snaps.

Figure 14:
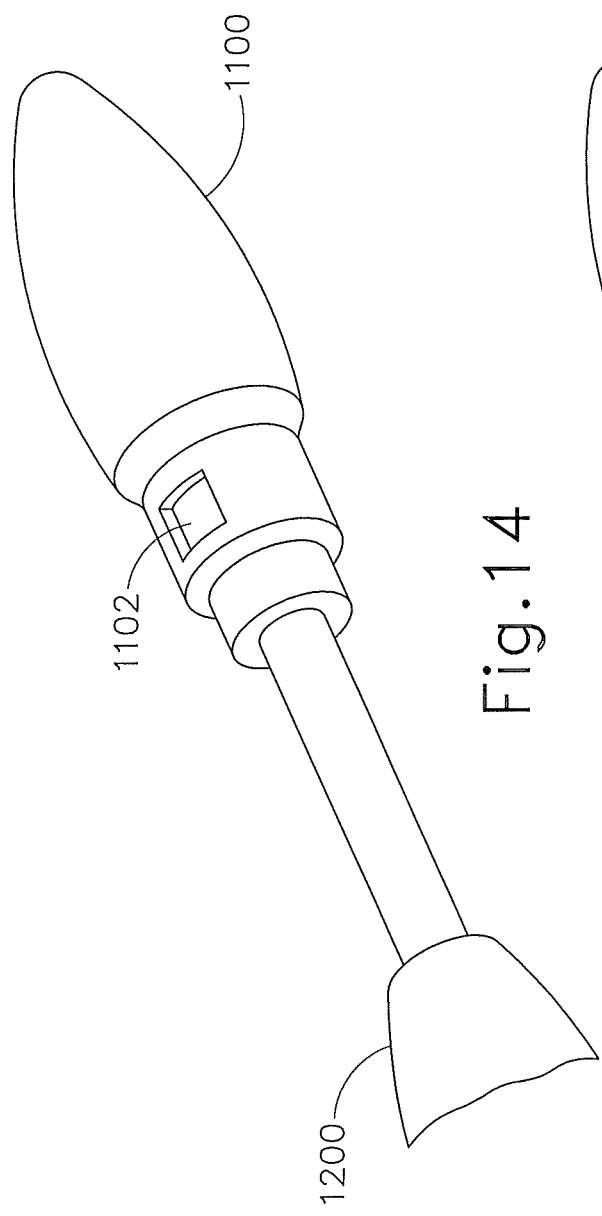
FIG. 14 depicts a perspective view of an exemplary torque wrench around an effector assembly, with an indicator window in the torque wrench.
Figure 15:
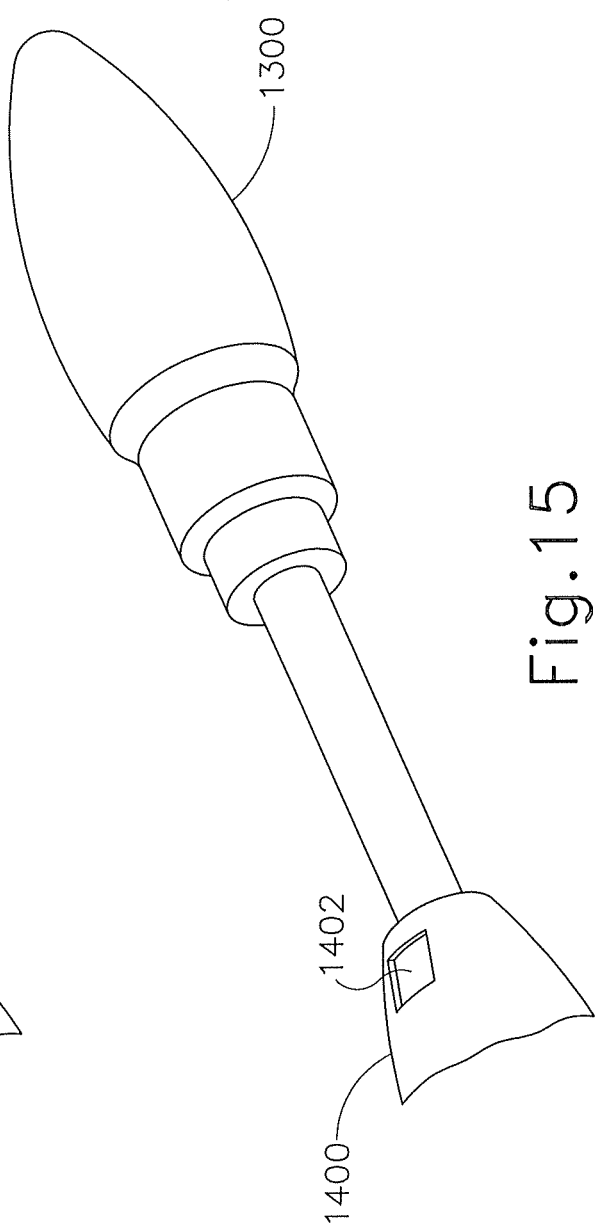
FIG. 15 depicts a perspective view of another exemplary torque wrench around an end effector assembly, with an indicator window in a surgical instrument handpiece.

As shown in FIG. 14, a torque attachment device (1100) may further include a window (1102). Torque attachment device (1100) may be used to rotate and attach a transmission assembly or end effector assembly to a transducer assembly (not shown) within a handle assembly (1200). Initially, window (1102) may show a red color, or any other suitable color, to indicate that transmission assembly or end effector assembly is not properly connected to the transducer assembly. Once a sufficient amount of torque is reached, torque attachment device (1100) may release force to the transmission assembly or end effector assembly. Torque attachment device (1100) may continue to rotate without rotating transmission assembly or end effector assembly. As torque attachment device (1100) rotates over transmission assembly or end effector assembly, window (1102) may show a green color, or other suitable color that is different from the initial color, to indicate that transmission assembly or end effector assembly is properly threaded to the transducer assembly. Coloring may be provided on the transmission assembly or end effector assembly such that window (1102) slides around transmission assembly or end effector assembly after a sufficient amount of torque are reached to show a different color through window (1102). As shown in FIG. 15, window (1402) may also be provided on handle assembly (1400) instead of torque attachment device (1300). Other suitable coloring methods will be apparent to one with ordinary skill in the art based on the teachings herein.

F. Exemplary Attachment Device Container

As noted above, some surgical instrument handpieces may be compatible with different kinds of shafts, end effectors, transmission assemblies, etc. In some instances, it may be beneficial to have such modular components readily available on hand for rapid exchange or replacement (e.g. in an operating room, etc.). To that end, FIGS. 16A and 16B depict an exemplary attachment device container (1500). Attachment device container (1500) comprises a plurality of receptacles (1502) configured to hold an attachment device (1600). Receptacles (1502) are configured to hold an attachment device (1600) with a transmission assembly or end effector assembly inside, or merely a transmission assembly or end effector assembly. The transmission assembly or end effector assembly is positioned in a receptacle (1502) so that the proximal opening is not obstructed and is ready to receive a handle assembly (1700). In the present example, receptacle (1502) is positioned to enclose attachment device (1600) in a vertical position. However, receptacle (1502) may hold attachment device (1600) in a horizontal or other angular position. Receptacle (1502) may also not fully enclose attachment device (1600) in some versions. Container (1500) may have a single receptacle (1502) or multiple receptacles (1502). As shown in FIG. 16B, handle assembly (1700) may be placed within receptacle (1502) to be threaded to a transmission assembly or end effector assembly. A user may also remove attachment device (1600) from container (1500) before assembly. Other variations will be apparent to one with ordinary skill in the art in view of the teachings herein.

For instance, a motor may be placed within receptacle (1502) to automate coupling between handle assembly (1700) and a transmission assembly or end effector assembly. As handle assembly (1700) is placed at receptacle (1502), a switch at the opening of receptacle (1502) may activate a motor to automatically couple handle assembly (1700) to a transmission assembly or end effector assembly in receptacle (1502). A switch may also be placed at the distal end of receptacle (1502), such that the switch activates a motor as handle assembly (1700) enters receptacle (1502) for coupling and depresses a transmission assembly or end effector assembly into receptacle (1502) and onto the switch. Other suitable methods to detect handle assembly (1700) at receptacle (1502) will be apparent to one with ordinary skill in the art in view of the teachings herein.

As noted above, many types of shafts, end effectors, transmission assemblies, etc., may be placed into container (1500). These different types may provide selectability among different shaft lengths, different surgical modalities (e.g. ultrasonic, RF electrosurgery, stapling, clipping, grasping, etc.), and/or other characteristics. Container (1500) may include a selector for a user to choose which application to couple to handle assembly (1700). A selector may rotate over receptacles (1502) to uncover a single receptacle (1502) and cover the remaining receptacles (1502). This allows a user to properly select the desired application to couple to handle assembly (1700). Once the user is finished with the desired application, an eject button on handle assembly (1700) may allow a user to decouple handle assembly (1700) with the transmission assembly or end effector. For instance, the user may eject a transmission assembly or end effector back into a receptacle (1502) of container (1500).

IV. Miscellaneous

It is contemplated that various teachings herein may be combined in numerous ways, and it should be understood that none of the teachings herein are intended to represent the limits of the inventors' contemplation. Various other examples of how several features of the surgical instruments described herein may be carried out in practice will be apparent to those of ordinary skill in the art in view of the teachings herein, and those examples are well within the inventors' contemplation.

By way of example only, at least a portion of handle assembly (60, 300, 800, 1000, 1200, 1400, 1700), transmission assembly (70, 680, 780, 980), and/or other components referred to herein may be constructed in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. Nos. 6,500,176; 7,416,101; 7,738,971; U.S. Pat. Pub. No. 2009/0209990, now U.S. Pat. No. 8,657,174; U.S. Pat. Pub. No. 2010/0069940, U.S. Pat. No. 9,023,071; Pub. No. 2011/0087218, now U.S. Pat. No. 8,939,974; U.S. Pat. Pub. No. 2009/0143797, now U.S. Pat. No. 8,419,757; and U.S. Pat. No. 6,783,524, the disclosures of which are herein incorporated by reference.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the present invention have application in conventional endoscopic and open surgical instrumentation as well as application in robotic-assisted surgery. An exemplary robotic-assist surgery systems is disclosed in U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body assembly, comprising:
      (i) an activation member,
      (ii) a first coupling assembly portion in communication with the activation member; and
   (b) an end effector assembly, comprising:
      (i) a transmission assembly,
      (ii) an end effector coupled to a distal end of the transmission assembly, and
      (iii) a second coupling assembly portion, wherein the second coupling assembly portion is operable to detachably couple to the first coupling assembly portion, wherein the activation member is operable to drive the end effector when the first and second coupling assembly portions are coupled;
   (c) an attachment assembly operable to rotatably couple the first coupling assembly portion to the second coupling assembly portion, wherein the attachment assembly is coupled to the second coupling assembly and is operable to indicate when the first coupling assembly is coupled to the second coupling assembly,
   wherein the attachment assembly includes a torque assembly, wherein the torque assembly is operable to prevent removal of the attachment assembly from the second coupling assembly before the second coupling assembly is coupled to the first coupling assembly.

2. The surgical instrument of claim 1, wherein the attachment assembly is coupled to the first coupling assembly.

3. The surgical instrument of claim 2, wherein the attachment assembly further comprises a motor operable to rotate the first coupling assembly relative to the body assembly.

4. The surgical instrument of claim 3, wherein the body assembly further comprises a casing, wherein the activation member further comprises a transducer assembly, wherein the first coupling assembly is at the distal end of the transducer assembly, wherein the motor is operable to rotate the transducer assembly relative to the casing.

5. The surgical instrument of claim 4, wherein the motor comprises an inner rotor and an outer stator, wherein the inner rotor rotates relative to the outer stator, wherein the inner rotor is coupled to the transducer assembly.

6. The surgical instrument of claim 1, wherein the attachment assembly comprises a proximal aperture, wherein the end effector assembly is contained within the attachment assembly, wherein the second coupling assembly is positioned at the proximal aperture.

7. The surgical instrument of claim 6, wherein the attachment assembly is operable to detect when the second coupling assembly is coupled to the first coupling assembly by transmitting a predetermined signal through the second coupling assembly.

8. The surgical instrument of claim 7, wherein the attachment assembly comprises a locking member, wherein the second coupling assembly comprises a shaft, wherein the shaft comprises a keyed portion, wherein the locking member is insertable into keyed portion and is thereby operable to prevent the first coupling assembly from rotating.

9. The surgical instrument of claim 8, wherein the first coupling assembly comprises a cartridge operable to insert locking member into keyed portion.

10. The surgical instrument of claim 7, wherein the attachment assembly comprises a resiliently biased transducer operable to send an acoustic waveform through the second coupling assembly.

11. The surgical instrument of claim 6, wherein the torque assembly is operable to prevent rotation of the first coupling assembly when the second coupling assembly is coupled to the first coupling assembly.

12. The surgical instrument of claim 11, wherein the attachment assembly comprises a battery operated motor.

13. The surgical instrument of claim 12, wherein the attachment assembly is operable to automatically activate the motor to rotate the second coupling assembly when the first coupling assembly is inserted into the proximal aperture.

14. The surgical instrument of claim 1, wherein the attachment assembly is operable to audibly indicate when the first coupling assembly is coupled to the second coupling assembly.

15. The surgical instrument of claim 1, wherein the attachment assembly is operable to visually indicate when the first coupling assembly is coupled to the second coupling assembly.

16. The surgical instrument of claim 15, wherein the attachment assembly comprises a shaft, wherein the shaft is colored by one color on a first side, wherein the shaft is colored by a second color on a second side, wherein the attachment assembly comprises a window, wherein the window is above the shaft, wherein the window rotates relative to shaft to visually indicate when the first coupling assembly is coupled to the second coupling assembly.

17. The surgical instrument of claim 1, wherein the attachment assembly further comprises a container, wherein the container comprises a receptacle operable to hold the end effector assembly such that the first coupling assembly is configured in the aperture to be coupled to the second coupling assembly.

18. A surgical instrument comprising:
   (a) a body assembly, comprising:
      (i) an activation member,
      (ii) a transducer assembly,
      (iii) a first coupling assembly portion in communication with the activation member, wherein the first coupling assembly is at a distal portion of the transducer assembly; and
   (b) an end effector assembly, comprising:
      (i) a transmission assembly,
      (ii) an end effector coupled to a distal end of the transmission assembly, and
      (iii) a second coupling assembly portion, wherein the second coupling assembly portion is operable to detachably couple to the first coupling assembly portion, wherein the activation member is operable to drive the end effector when the first and second coupling assembly portions are coupled;
(c) an attachment assembly comprising a proximal aperture and enclosing a remainder of the end effector assembly, wherein the attachment assembly is operable to rotate the second coupling assembly relative to the first coupling assembly portion, wherein the attachment assembly is operable to indicate when the first coupling assembly is coupled to the second coupling assembly.

19. The surgical instrument of claim 18, wherein the attachment assembly comprises a sensor configured to detect when the second coupling assembly is coupled to the first coupling assembly by detecting a predetermined resonance of the first and second couplings.

20. A surgical instrument comprising:
(a) a body assembly, comprising:
 (i) an activation member,
 (ii) a first coupling assembly portion in communication with the activation member; and
(b) an end effector assembly, comprising:
 (i) a transmission assembly,
 (ii) an end effector coupled to a distal end of the transmission assembly, and
 (iii) a second coupling assembly portion, wherein the second coupling assembly portion is operable to detachably couple to the first coupling assembly portion, wherein the activation member is operable to drive the end effector when the first and second coupling assembly portions are coupled;
(c) an attachment assembly operable to rotatably couple the first coupling assembly portion to the second coupling assembly portion, wherein the attachment assembly is operable to indicate when the first coupling assembly is coupled to the second coupling assembly, wherein the attachment assembly is coupled to the first coupling assembly, wherein the attachment assembly further comprises a motor operable to rotate the first coupling assembly relative to the body assembly.

* * * * *